(12) United States Patent
Chen et al.

(10) Patent No.: US 10,488,352 B2
(45) Date of Patent: Nov. 26, 2019

(54) HIGH SPATIAL RESOLUTION NUCLEAR MAGNETIC RESONANCE LOGGING

(71) Applicant: Saudi Arabian Oil Company, Dhahran (SA)

(72) Inventors: Jin-Hong Chen, Katy, TX (US); Stacey M. Althaus, Houston, TX (US); Mohammad Delshad, Houston, TX (US); Yang Zhao, Katy, TX (US)

(73) Assignee: Saudi Arabian Oil Company, Dhahran (SA)

( * ) Notice: Subject to any disclaimer, the term of this patent is extended or adjusted under 35 U.S.C. 154(b) by 124 days.

(21) Appl. No.: 15/873,576

(22) Filed: Jan. 17, 2018

(65) Prior Publication Data

US 2018/0217073 A1    Aug. 2, 2018

Related U.S. Application Data

(60) Provisional application No. 62/451,262, filed on Jan. 27, 2017, provisional application No. 62/531,038, filed on Jul. 11, 2017.

(51) Int. Cl.
*G01N 24/08*    (2006.01)
*G01R 33/24*    (2006.01)
(Continued)

(52) U.S. Cl.
CPC ......... *G01N 24/081* (2013.01); *G01R 33/246* (2013.01); *G01R 33/307* (2013.01);
(Continued)

(58) Field of Classification Search
CPC ........ G01R 33/34084; G01R 33/34092; G01R 33/445; G01R 33/246; G01R 33/307;
(Continued)

(56) References Cited

U.S. PATENT DOCUMENTS 2,913,658 A    11/1959  Theodore
4,480,227 A *  10/1984  Brown ............... G01V 3/32
                                                       324/303

(Continued)

OTHER PUBLICATIONS

Pierens et al., "Quantitative longitudinal fluid saturation profiles with a slice-selected CPMG sequence," Magnetic Resonance Imaging, Elsevier Science, vol. 12, No. 2, Jan. 1, 1994.

(Continued)

*Primary Examiner* — Patrick Assouad
*Assistant Examiner* — Demetrius R Pretlow
(74) *Attorney, Agent, or Firm* — Fish & Richardson P.C.

(57) ABSTRACT

Certain techniques for Nuclear Magnetic Resonance (NMR) whole core logging are described. NMR tests are performed on a standard sample using a NMR radio frequency (rf) coil having a length. A response map of the NMR rf coil is determined. The response map relates multiple relative NMR rf coil positions to multiple relative signal intensities. The NMR tests are performed using the NMR rf coil on a rock sample containing fluid. A length of the rock sample is greater than the NMR rf coil. Fluid content in the sample is determined using results of the NMR tests using the NMR rf coil on the rock sample and using the response map for the NMR rf coil and a mathematical deconvolution to obtain high resolution. The same method can be used to obtain high spatial resolution NMR log measurement in the reservoir.

24 Claims, 20 Drawing Sheets

(51) Int. Cl.
*G01V 3/32* (2006.01)
*G01R 33/34* (2006.01)
*G01R 33/46* (2006.01)
*G01R 33/30* (2006.01)

(52) U.S. Cl.
CPC ... *G01R 33/34046* (2013.01); *G01R 33/4625* (2013.01); *G01V 3/32* (2013.01)

(58) Field of Classification Search
CPC ......... G01R 33/34046–34076; G01R 33/4625; G01N 24/081; G01V 3/32
See application file for complete search history.

(56) References Cited

U.S. PATENT DOCUMENTS

| | | | | |
|---|---|---|---|---|
| 4,542,343 | A * | 9/1985 | Brown | G01R 33/46 324/307 |
| 5,304,930 | A * | 4/1994 | Crowley | G01R 33/3808 324/309 |
| 5,565,775 | A * | 10/1996 | Stallmach | G01V 3/14 324/303 |
| 6,570,382 | B1 * | 5/2003 | Hurlimann | G01N 24/081 324/303 |
| 8,653,815 | B2 | 2/2014 | Chanpura et al. | |
| 8,686,724 | B2 * | 4/2014 | Mitchell | G01N 24/081 324/303 |
| 8,791,695 | B2 | 7/2014 | Balcom et al. | |
| 8,890,527 | B1 * | 11/2014 | Balcom | G01R 33/5659 324/307 |
| 9,389,193 | B1 | 7/2016 | Petrov et al. | |
| 9,507,047 | B1 * | 11/2016 | Dvorkin | G01V 5/101 |
| 10,061,048 | B2 * | 8/2018 | Song | G01V 3/14 |
| 2001/0028247 | A1 * | 10/2001 | King | G01R 33/60 324/312 |
| 2002/0105326 | A1 * | 8/2002 | Hurlimann | G01V 3/32 324/303 |
| 2003/0197506 | A1 * | 10/2003 | Song | G01N 24/081 324/303 |
| 2006/0097722 | A1 * | 5/2006 | Scheven | G01N 24/081 324/303 |
| 2006/0132131 | A1 * | 6/2006 | Fleury | G01N 15/0826 324/307 |
| 2008/0150524 | A1 * | 6/2008 | Song | G01N 24/081 324/303 |
| 2009/0125239 | A1 * | 5/2009 | Niemeyer | G01N 24/081 702/11 |
| 2010/0010744 | A1 * | 1/2010 | Prange | G01V 3/32 702/7 |
| 2010/0109664 | A1 * | 5/2010 | Minh | G01V 3/32 324/303 |
| 2014/0157870 | A1 * | 6/2014 | Kornacki | G01N 33/241 73/23.38 |
| 2014/0285196 | A1 * | 9/2014 | Liu | G01N 24/081 324/309 |
| 2016/0161630 | A1 * | 6/2016 | Badri | G01V 3/32 324/303 |
| 2017/0139027 | A1 * | 5/2017 | Nicot | G01N 24/081 |
| 2019/0086312 | A1 * | 3/2019 | Kwak | G01N 24/082 |

OTHER PUBLICATIONS

Vashee et al., "B1 mapping with a pure phase encode approach: Quantitative density profiling,"Journal of Magnetic Resonance vol. 232, May 1, 2013, 8 pages.

Cory et al., "NMR imaging of soilds with a spatially selective receiver coil," Measurement Science and Technology, IOP, Bristol, GB, Dec. 1, 1990, 5 pages.

Jin-Hong Chen et al., "Enhanced Spatial Resolution of Magnetic Resonance Measurement and Application to Whole Core Shale," presented at the SCA2017-065 at the International Symposium of the Society of Core Analysts, Vienna, Austria, Aug. 27-Sep. 1, 2017, 9 pages.

International Search Report and Written Opinion issued in International Application No. PCT/US2018/014481 dated Jun. 27, 2018, 24 pages.

Carr et al., "Effects of Diffusion on Free Precession in Nuclear Magnetic Resonance Experiments," Physical review 94(3), May 1, 1954, 13 pages.

Meiboom et al., "Modified Spin-Echo Method for Measuring Nuclear Relaxation Times," Review of Scientific Instruments vol. 29, No. 8, Aug. 1958, 5 pages.

Provencher, "A constrained regularization mathod for inverting data represented by linear algebraic or integral equations," Computer Physics Communications, vol. 27, Issue 3, North-Holland Publishing Company, Sep. 1982, 15 pages.

Vogel, "Computational Methods for Inverse Problems, Chapter 2: Analytical Tools," Society for Industrial and Applied Mathematics, 2002, 2 pages.

Rauschhuber, "Profiling of Relaxation Time and Diffusivity Distributions with Low Field NMR," Thesis submitted at Rice University, Apr. 2011, 140 pages.

Vashaee et al., "Local T2 Measurement Employing Longitudinal Hadmard Encoding and Adiabatic Inversion Pulses in Porous Media," Journal of Magnetic Resonance vol. 261, Dec. 2015, 8 pages.

Vashaee et al., "A comparison of magnetic resonance methods for spatially resolved $T_2$ distribution measurements in porous media," IOP Publishing, Measurement Science Technology vol. 26, Apr. 2015, 17 pages.

Vashaee et al., "Region of interest selection of long core plug samples by magnetic resonance imaging: profiling and local $T_2$ measurement," IOP Publishing, Measurement Science Technology vol. 25, Feb. 2014, 12 pages.

* cited by examiner

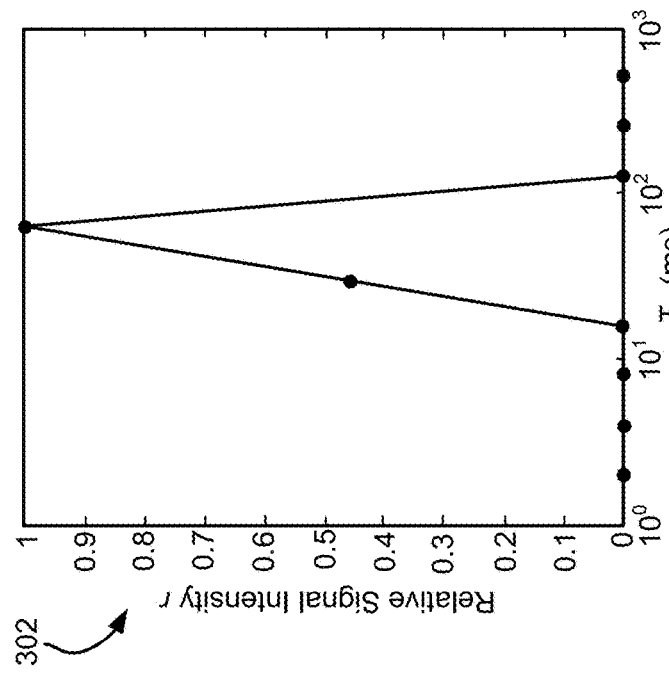
FIG. 3B
FIG. 3A
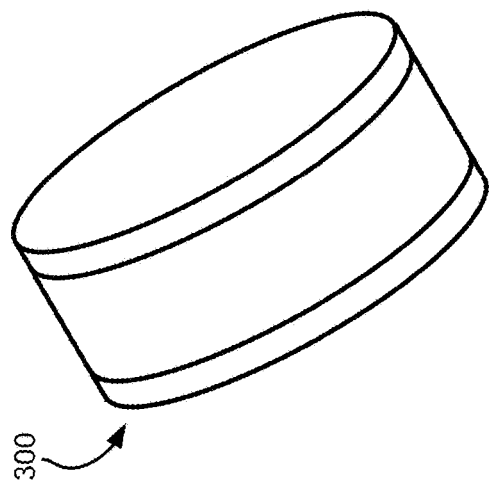
| Relative Position | 0 | 1 | 2 | 3 | 4 | 5 | 6 |
|---|---|---|---|---|---|---|---|
| Relative Signal Intensity $r$ | 0.01 | 0.35 | 1.00 | 0.98 | 0.98 | 0.49 | 0.05 |
FIG. 3C

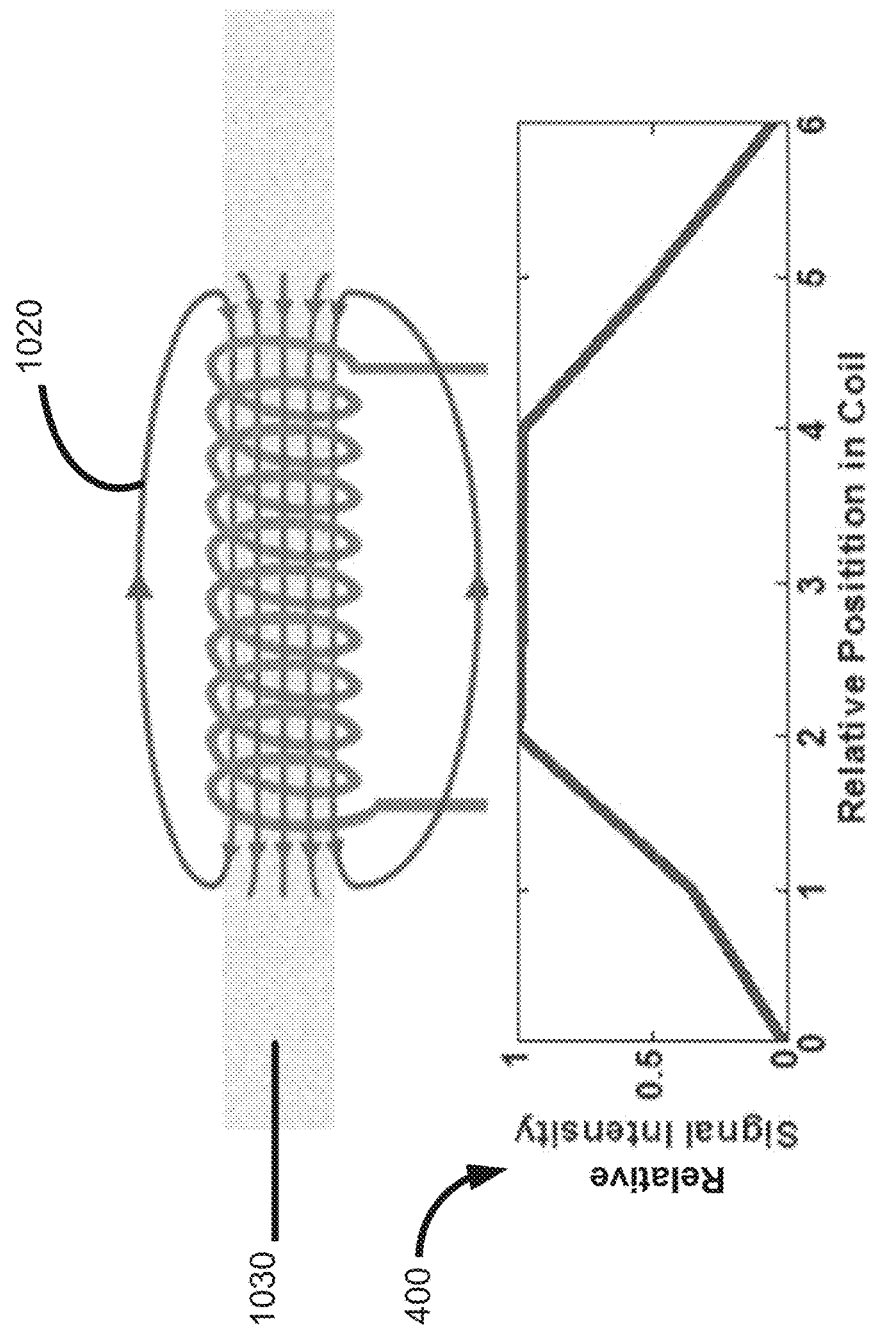

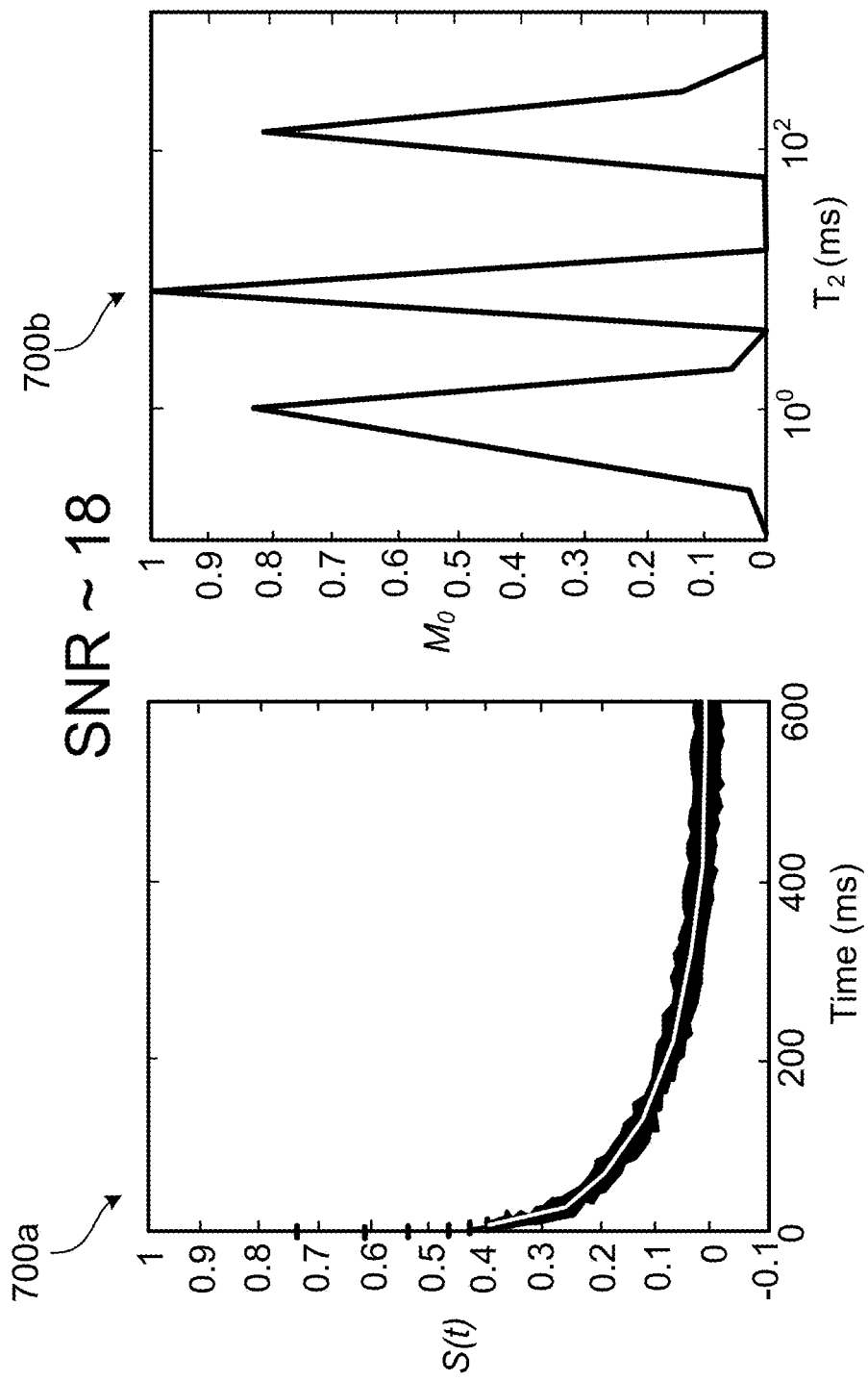

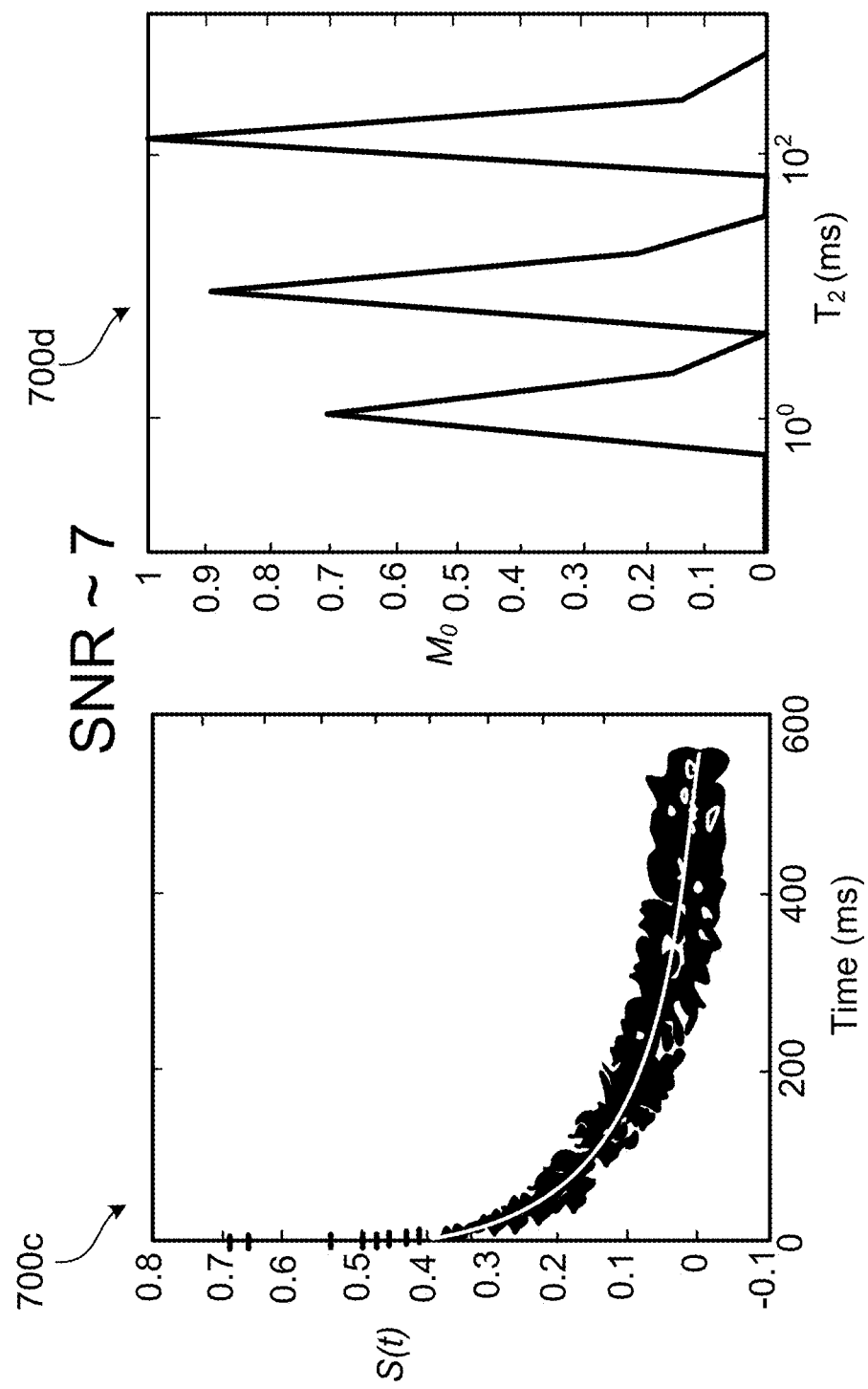

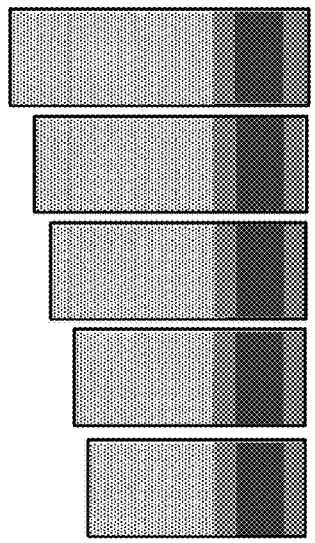
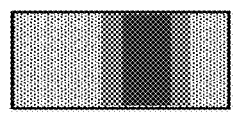
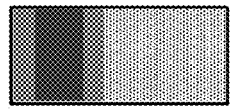
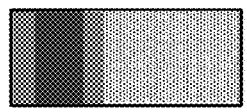
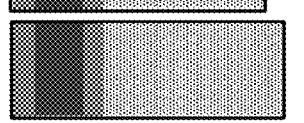
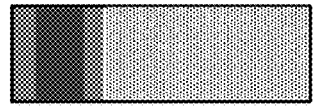
FIG. 8
$S_1 = r_1 a_1$
$S_2 = r_1 a_2 + r_2 a_1$
$S_3 = r_1 a_3 + r_2 a_2 + r_3 a_1$
$S_4 = r_1 a_4 + r_2 a_3 + r_3 a_2 + r_4 a_1$
$S_5 = r_1 a_5 + r_2 a_4 + r_3 a_3 + r_4 a_2 + r_5 a_1$
$S_n = r_1 a_n + r_2 a_{n-1} + r_3 a_{n-2} + r_4 a_{n-3} + r_5 a_{n-4}$
$S_k = r_1 a_k + r_2 a_{k-1} + r_3 a_{k-2} + r_4 a_{k-3} + r_5 a_{k-4}$
$S_{k+1} = r_2 a_k + r_3 a_{k-1} + r_4 a_{k-2} + r_5 a_{k-3}$
$S_{k+1} = r_3 a_k + r_4 a_{k-1} + r_5 a_{k-2}$
$S_{k+3} = r_4 a_k + r_5 a_{k-1}$
$S_{k+3} = r_5 a_k$

HIGH SPATIAL RESOLUTION NUCLEAR MAGNETIC RESONANCE LOGGING

CROSS-REFERENCE TO RELATED APPLICATION(S)

This application claims the benefit of priority to U.S. Provisional Application Ser. No. 62/451,262, filed Jan. 27, 2017 and U.S. Provisional Application Ser. No. 62/531,038, filed Jul. 11, 2017, the contents of which are hereby incorporated by reference.

TECHNICAL FIELD

This specification relates to measuring, for example, Nuclear Magnetic Resonance (NMR) measurement of rock samples, for example, core samples retrieved from geologic formations, and NMR measurement of formations in the reservoir.

BACKGROUND

Horizontal drilling and hydraulic fracturing have improved hydrocarbon production from unconventional shale reservoirs and other tight reservoirs. To predict hydrocarbon production and to optimize production strategy from such reservoirs, understanding the hydrocarbon storage and transport mechanisms is beneficial. Low field NMR has proven to be a powerful logging technology for measuring fluid content and other properties in a geologic formation, for example, a hydrocarbon-bearing reservoir, and for characterizing fluid-solid interaction. It has also been used in the laboratory for accurate characterization of petroleum systems and for calibration of field log data.

SUMMARY

This specification describes technologies relating to NMR measurement with improved high spatial resolution of rock cores including whole cores in laboratory and of formations in reservoirs. Resolution refers to the ability to resolve small and thin features.

Certain aspects of the subject matter described here can be implemented as a method. Nuclear Magnetic Resonance (NMR) tests are performed on a standard sample using a NMR radio frequency (rf) coil having a finite length. A response map of the NMR rf coil is determined. The response map relates to multiple signal intensities at different positions relative to the NMR rf coil. Each respective signal intensity corresponds to a relative NMR rf coil position. In one dimension, the NMR rf coil has a characteristic response map which can be approximated by a trapezoid or Gaussian with characteristic width. The NMR tests are performed using the NMR rf coil on a rock sample containing fluid. A length of the rock sample is greater than the NMR rf coil. A fluid content in the rock sample is determined using results of the NMR tests using the NMR rf coil on the rock sample and using the response map for the NMR rf coil.

This, and other aspects, can include one or more of the following features. The length of the standard sample can be less than the length of the NMR rf coil. The standard sample can have a known content of fluid. The NMR tests can be performed at multiple relative NMR rf coil positions by, at each position, (a) positioning the standard sample at a relative NMR rf coil position, (b) exposing the standard sample to an electromagnetic field, and (c) measuring a signal induced in the coil in response to the electromagnetic field, the signal corresponds to the known content of the fluid in the standard sample and the relative NMR rf coil position at which the standard sample is positioned. The standard sample can be moved relative to the NMR rf coil to a subsequent NMR rf coil position, and the steps (a), (b) and (c) can be repeated.

The standard sample can be moved automatically using a step motor.

A distance by which the standard sample is moved within the NMR rf coil corresponds to a resolution at which the fluid content in the rock sample is determined.

To determine the response map for the NMR rf coil, the relative NMR rf coil positions and the multiple relative signal intensities can be stored in a computer-readable storage medium.

To perform the NMR measurements using the NMR rf coil on the rock sample containing the fluid, the operations performed include, at each position, (d) positioning the rock sample within the NMR rf coil at a relative NMR rf coil position, (e) exposing the rock sample to the electromagnetic field, and (f) measuring the signal induced in the coil in response to the electromagnetic field, the signal corresponding to the fluid content in the rock sample and the relative NMR rf coil position at which the rock sample is positioned.

The rock sample can be moved along the NMR rf coil to the subsequent NMR rf coil position, and the steps (d), (e) and (f) can be repeated.

The rock sample can be moved automatically using a step motor.

A distance by which the rock sample is moved within the NMR rf coil can correspond to a resolution at which the NMR rf coil determines the fluid content in the rock sample.

In order to determine the fluid content in the rock sample using NMR measurements on the rock sample and using the NMR rf coil response map, a post-processing protocol can be implemented on multiple signal values measured at multiple NMR rf coil positions at which the rock sample was place. The post-processing protocol can implement the multiple relative signal intensities measured at the multiple NMR rf coil positions using the standard sample.

To implement the post-processing protocol, the multiple signal values can be represented in matrix form as S=RA. S represents the multiple signal values, R represents the multiple relative signal intensities related to the response map of the rf coil, and A represents the fluid content within the rock with high spatial resolution. The fluid content, A, can be determined by implementing matrix-inversion and deconvolution methods $A=R^{-1}S$. The same method can be used on NMR log data to obtain high spatial resolution logs.

To implement the post-processing protocol, the multiple signal values can be represented in matrix form as S=RA. S represents the multiple signal values, R represents the multiple relative signal intensities related to the response map of the rf coil, and A represents the fluid content within the rock with high spatial resolution. The fluid content, A, can be determined by implementing convex minimization of an objective function.

Certain aspects of the subject matter described here can be implemented as a computer-implemented method. The method includes receiving a response map of a Nuclear Magnetic Resonance (NMR) radio frequency (rf) coil. The response map is determined using NMR tests performed on a standard sample having a known length and fluid content using the NMR rf coil. The response map relates multiple relative NMR rf coil positions to multiple relative signal intensities. Each relative NMR rf coil position corresponds to a respective relative signal intensity. The method includes receiving multiple signal values determined by performing the NMR tests using the NMR rf coil on a rock sample containing fluid. The length of the rock sample can be greater than the NMR rf coil. The NMR tests on the rock sample are performed by moving the rock sample within and relative to the NMR rf coil. The method includes determining a fluid content in the rock sample using the plurality of signal values and the response map.

This, and other aspects, can include one or more of the following features. In order to determine the fluid content in the rock sample using the multiple signal values and the response map, a post-processing protocol can be implemented on the multiple signal values. The post-processing protocol can implement the multiple relative signal intensities measured at the multiple NMR rf coil positions using the standard sample.

To implement the post-processing protocol, the multiple signal values can be represented in matrix form as S=RA. S represents the multiple signal values, R represents the multiple relative signal intensities related to the response map of the rf coil, and A represents the fluid content within the rock with high spatial resolution. The fluid content, A, can be determined by implementing matrix-inversion.

To implement the post-processing protocol, the multiple signal values can be represented in matrix form as S=RA. S represents the multiple signal values, R represents the multiple relative signal intensities related to the response map of the rf coil, and A represents the fluid content within the rock with high spatial resolution. The fluid content, A, can be determined by implementing convex minimization of an objective function.

Certain aspects of the subject matter described here can be implemented as a system that includes an NMR system configured to perform NMR tests on samples. The NMR system includes an NMR rf coil configured to move relative to a sample to determine NMR signal values responsive to electromagnetic fields to which the sample is exposed. The system includes a computer system including one or more processors and a computer-readable storage medium storing instructions executable by the one or more processors to perform operations described in this specification. The operations include receiving a response map of the NMR rf coil. The response map is determined using NMR tests performed by the NMR system on a standard sample having a known length and fluid content. The response map relates multiple relative NMR rf coil positions to multiple relative signal intensities, where each relative NMR rf coil position corresponds to a respective relative signal intensity. The operations include receiving multiple signal values determined by performing the NMR tests using the NMR system on a rock sample which contains fluid. A length of the rock sample is greater than the NMR rf coil, and the NMR tests on the rock sample are performed by moving the rock sample within and relative to the NMR rf coil. The operations include determining a fluid content in the rock sample using the multiple signal values and the response map.

This, and other aspects, can include one or more of the following features. In order to determine the fluid content in the rock sample using the multiple signal values and the response map, a post-processing protocol can be implemented on the multiple signal values. The post-processing protocol can implement the multiple relative signal intensities measured at the multiple NMR rf coil positions using the standard sample.

To implement the post-processing protocol, the multiple signal values can be represented in matrix form as S=RA. S represents the multiple signal values, R represents the multiple relative signal intensities related to the response map of the rf coil, and A represents the fluid content within the rock with high spatial resolution. The fluid content, A, can be determined by implementing matrix-inversion.

To implement the post-processing protocol, the multiple signal values can be represented in matrix form as S=RA. S represents the multiple signal values, R represents the multiple relative signal intensities related to the response map of the rf coil, and A represents the fluid content within the rock with high spatial resolution. The fluid content, A, can be determined by implementing convex minimization of an objective function.

A length of the standard sample can be less than the length of the NMR rf coil. The NMR system can be configured to perform the NMR tests on the standard sample using the NMR rf coil by (a) positioning the standard sample at a relative NMR rf coil position, (b) exposing the standard sample to an electromagnetic field, and (c) measuring a signal induced in the coil in response to the electromagnetic field. The signal corresponds to the known content of the fluid in the standard sample and the relative NMR rf coil position at which the standard sample is positioned. The signal corresponds to the relative signal intensity of the NMR rf coil position. The standard sample can be moved relative to the NMR rf coil to a subsequent NMR rf coil position, and the steps (a), (b) and (c) can be repeated.

The NMR system can be configured to perform the NMR tests using the NMR rf coil on the rock sample which contains the fluid by (d) positioning the rock sample within the NMR rf coil at a relative NMR rf coil position, (e) exposing the rock sample to the electromagnetic field, and (f) measuring the signal induced in the coil in response to the electromagnetic field. The signal corresponds to the fluid content in the rock sample and the relative NMR rf coil position at which the rock sample is positioned. The rock sample can be moved within the NMR rf coil to the subsequent NMR rf coil position, and the steps (d), (e) and (f) can be repeated.

A distance by which the rock sample is moved within the NMR rf coil can correspond to a resolution at which the NMR rf coil determines the fluid content in the rock sample.

The details of one or more implementations of the subject matter described in this specification are set forth in the accompanying drawings and the description that follows. Other features, aspects, and advantages of the subject matter will become apparent from the description, the drawings, and the claims.

DESCRIPTION OF DRAWINGS

FIG. 3A is a schematic diagram of a standard NMR sample.

FIG. 3B shows a $T_2$ spectrum of fluid in the standard NMR sample of FIG. 3A.

FIG. 3C is a response map table of relative signal intensities at respective standard NMR sample positions.

FIG. 4A is a schematic diagram of NMR data acquisition for a rock sample using the NMR test system.

FIG. 4B is a plot of signal intensity at different relative positions of the rock sample in a NMR rf coil of the NMR test system.

FIGS. 7A-7D show results of an inversion test on synthetic data.

FIG. 8 is a schematic illustration of a rock sample moving into a NMR rf coil and corresponding detected signals.

DETAILED DESCRIPTION

Figure 1:
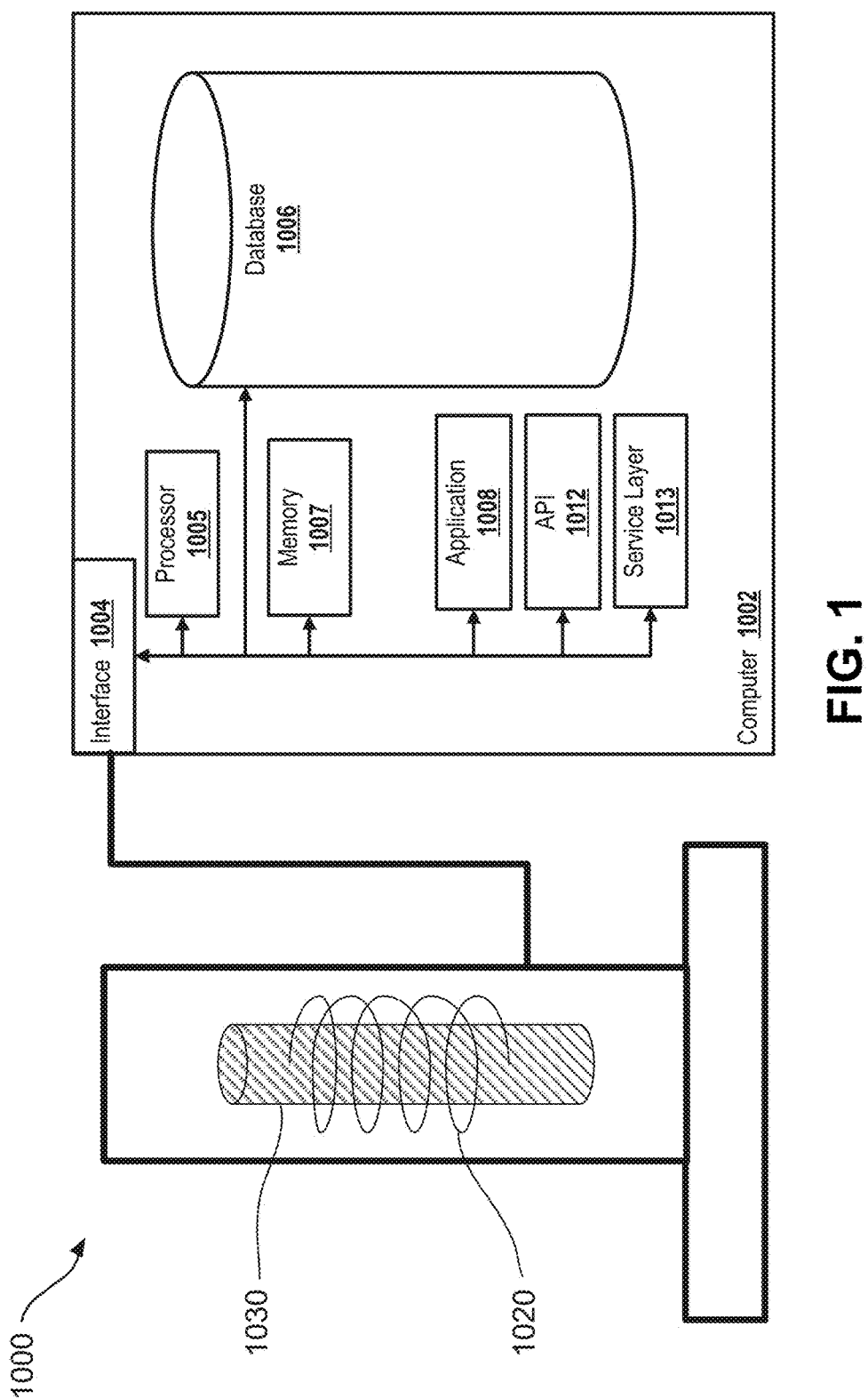
FIG. 1 is a schematic diagram of a NMR test system to determine fluid content of a rock sample.

Magnetic Resonance Imaging (MRI) and magnetic resonance spectroscopy (MRS) is used in many fields including, for example, medical diagnosis and evaluation, material assessment, formation evaluation, process control, and other fields. As described earlier, low-field (100 Kilohertz (kHz) to 30 Megahertz (MHz)) NMR has been applied to estimate fluid content and to characterize fluid transport properties for a reservoir. Low-field NMR has also been implemented in laboratories for fluids and small core plug analysis to increase accuracy of petrophysical measurements and for calibration of wellbore log data. A limiting factor of NMR application for whole core or well logging is that the spatial resolution is limited by the length of the NMR radio frequency (rf) coil. The length of the rf coil can be a few inches for a laboratory instrument, and a few inches to a few feet for well-logging tools, but the desired resolution can be only a fraction of the rf coil length.

For NMR measurements on long samples or log applications where the studied objects are always longer than the rf coil, the end effect of a finite-length coil becomes significant. Where the sample is shorter than the coil, the coil can be assumed to be infinite, meaning that the rf field strength and measurement sensitivity across the sample is homogeneous. However, coils are finite, and the rf field is not homogeneous, especially at the two ends of the coil. Consequently, end effects play a significant role when the sample is longer than the rf coil. The measured signal includes signal from the two ends, and also from the homogeneous part of the sample within the coil.

One solution to this problem of obtaining high resolution measurement is to use pulsed field gradient (PFG) technology for slice selection, a technique used in MRI. However, the cost of high quality PFG can be prohibitive. In addition, the technique cannot be used to quantitatively analyze materials with short transverse relaxation times, $T_2$, because the signal decays to a very small value during the application of PFG. Many tight rocks—referring to rocks with low permeability and small pores, for example, shales, tight sandstones, tight carbonates, and other tight rocks—have some $T_2$ of substantially 1 millisecond (ms) or less. In this specification, "substantially" means a deviation or allowance of up to 10 percent (%) and any variation from a mentioned value is within the tolerance limits of any machinery used to manufacture the part. If a PFG of 0.8 ms is used, the signal decays to exp(−0.8)=0.45 or smaller. In this case, more than half of the signal is lost, and more will be lost if a longer PFG is used.

This specification describes a method and workflow to acquire high spatial resolution NMR data for whole core logging and for reservoir NMR logging, for example, for organic-rich shales and other formations. The workflow can be implemented to obtain fluid content in a core sample, and to log whole cores obtained from different wellbores. A whole core sample is a rock sample retrieved from an unconventional reservoir (for example, a shale reservoir, tight sand, tight carbonate, or other tight reservoir). In such a sample, fluids (for example, liquids) remain in the rock due to nano-Darcy permeabilities of the porous sample network. The method and workflow described in this specification can be implemented to estimate fluid content and to characterize fluid-solid interaction in such whole core samples to reveal information about the unconventional reservoirs from which the whole core samples are retrieved.

The NMR whole core logging described in this specification can be used as a non-destructive tool to estimate fluid content in whole cores at well-sites or at core handling facilities, and can be combined with other whole core analyses, for example, continuous gamma ray measurements, for samples retrieved from unconventional reservoirs. The techniques described here can be implemented to provide a measurement of fluid content and images with any spatial resolution that is not limited by the length of the rf coil or antenna used in the measurement. The techniques can be particularly useful in laboratory applications for samples longer than the coil and in well-logging where the studied objects are longer than the tool antenna. The techniques account for, and thus, are not limited by the end effects of the finite length of the rf coil. The techniques can deliver quantitative images or measurement for material with very short relaxation time. The technique also offers the possibility of much quieter and cheaper MRI instruments by reducing the use of PFG for medical applications.

FIG. 1 is a schematic diagram of a NMR test system 1000 to determine fluid content of a rock sample. The system 1000 includes a NMR test apparatus including a NMR radio frequency (rf) coil 1020 into which a rock sample 1030, for example, a whole core sample can be positioned. An axial length of the NMR rf coil 1020 is less than that of the rock sample 1030. A diameter of the NMR rf coil 1020 is greater than that of the rock sample 1030. The NMR rf coil 1020 and the rock sample 1030 can be axially moved relative to each other in a step-wise movement described later. At each step, the NMR test is performed on the rock sample 1030 by exposing the rock sample 1030 to an electromagnetic field, which can induce a current in the NMR rf coil 1020. A quantity of current induced in the NMR rf coil 1020 is a function of the fluid content in the portion of the rock sample 1030 within the NMR rf coil 1020. By positioning each portion of the rock sample 1030 within the NMR rf coil 1020 and by performing the NMR test for each portion, multiple quantities of current, each corresponding to a respective portion along the longitudinal axis of the rock sample 1030 can be measured. A controlled relative movement of the samples relative to the NMR rf coil 1020 is important, as explained later.

The NMR test apparatus is connected to a computer system 1002, the details of which are described later. The computer system 1002 can include one or more processors and a computer-readable storage medium (for example, a computer-readable memory) to store instructions executable by the one or more processors, to perform operations. For example, the computer system 1002 can implement a post-processing protocol described to determine the fluid content in the rock sample 1030 from the multiple quantities of current measured as described earlier. As described later, the computer system 1002 can determine the fluid content at a resolution equal to the length of the NMR rf coil 1020 and further post-process the measured current to determine the fluid content at a resolution equal to a length of the step by which the NMR rf coil 1020 and the rock sample 1030 were moved relative to each other.

For certain example tests described later, the NMR rf coil 1020 had a length of 4.25 inches. Each rock sample was a whole core sample obtained from an unconventional reservoir. Each whole core sample had a diameter of 4 inches and a length of 12 inches. Each whole core sample was moved relative to the NMR rf coil 1020 in one-inch steps. The computer system 1002 determined the fluid content in each whole core sample at resolutions of substantially 4 inches (the length of the NMR rf coil 1020) and substantially 1 inch (the step length). To do so, the computer system 1002 implemented data inversion instructions and deconvolution instructions (both described later) for the measured data.

Figure 2:
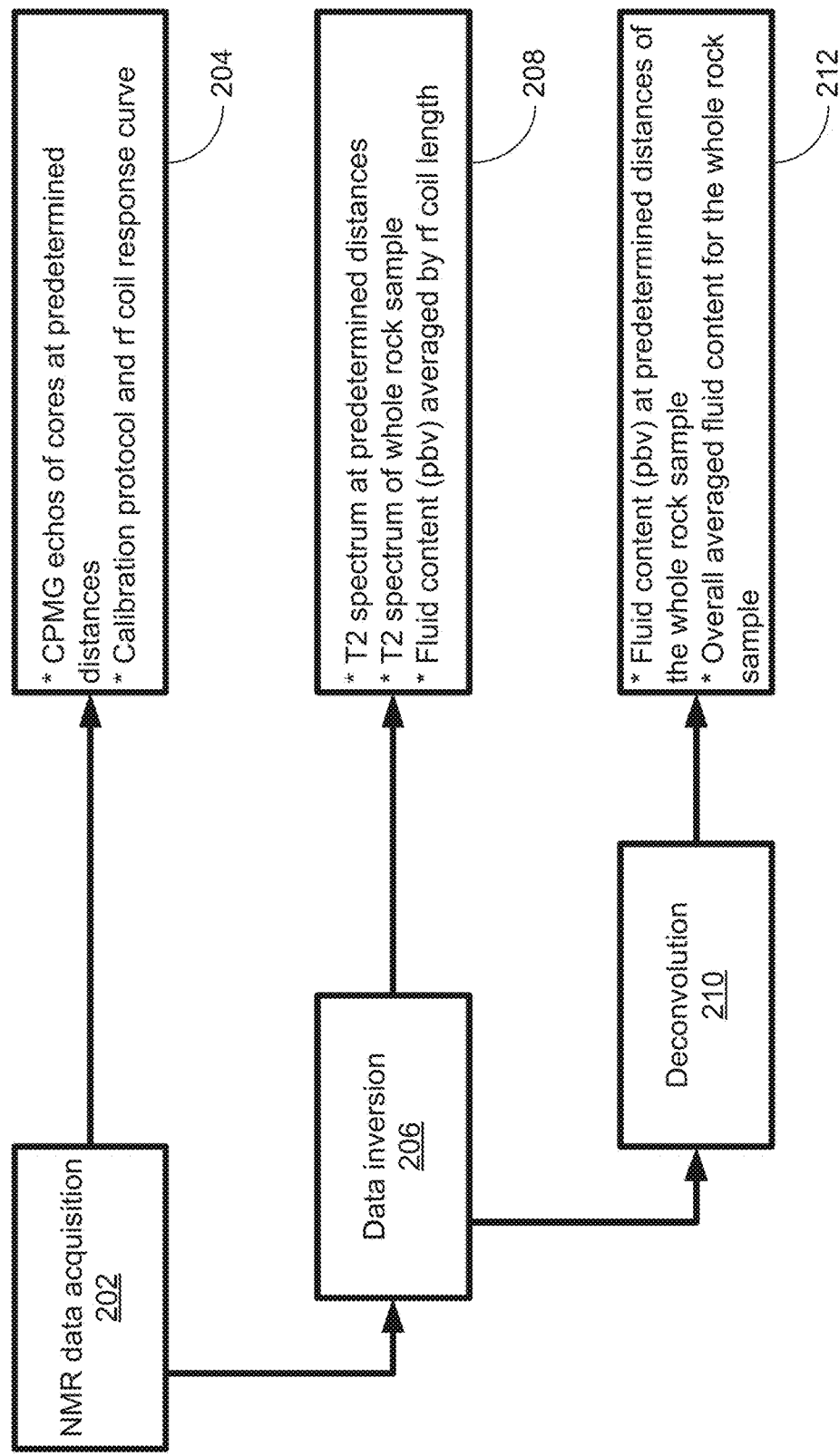
FIG. 2 is a workflow implemented by the NMR test system of FIG. 1.

FIG. 2 is a workflow implemented by the NMR test system 1000 of FIG. 1. The system 1000 first implements NMR data acquisition 202. The steps 204 of NMR data acquisition 202 include subjecting portions of the rock sample 1030 to Carr and Purcell, Meiboom and Gill (CPMG) pulse sequence echos of cores at predetermined distances, and implementing a calibration protocol to determine its response map (sometimes called a response curve) for the NMR rf coil 1020. The system 1000 next implements data inversion 206. The steps 208 of data inversion 206 include obtaining a $T_2$ spectrum at predetermined distances for the rock sample 1030, obtaining a $T_2$ spectrum of the rock sample 1030, and determining fluid content averaged by the NMR rf coil 1020, that is, at the resolution equal to or larger than the NMR rf coil 1020 length. The system 1000 next implements deconvolution 210. The steps 212 of deconvolution 210 include post-processing the data acquired by NMR data acquisition 202 to determine fluid content at predetermined distances of the rock sample 1030, and to determine overall averaged fluid content for the rock sample 1030. Details of each aspect of the workflow implemented by the system 1000 are described with reference to the figures that follow.

Obtaining Rock Samples

For certain example tests described, 35 whole core samples (each 12 inches long, with a 4-inch diameter) were obtained from wellbores. Each whole core sample was cut and transported to a laboratory in which the tests were performed in fiberglass sleeves or aluminum sleeves. Each whole core sample was radiographed by a computerized tomography (CT) scanner in as-received conditions. The whole core samples were then removed from their sleeves and packaged, for example, wrapped in heat-shrink Teflon™ with Teflon™ end-caps to protect the whole core samples from further damage. Almost all the whole core samples exhibited fractures along the beddings. Some whole core samples, for example, those with core plugs taken out, had larger and more fractures than others, and some whole core samples had moderate damage.

NMR Test Apparatus

For certain example tests described, the NMR test apparatus was an NMR spectrometer obtained from Ecotek Corporation (Houston, Tex., USA). The static magnetic field was 1.83 megahertz (MHz). The diameter of the NMR rf coil 1020 was 4.25 inches, allowing the 4-inch diameter whole core samples to be pushed through the magnet for NMR data acquisition. The whole core sample was not perfectly aligned or centered within the NMR rf coil 1020 and had some space left on the top while resting on the bottom of the opening of the NMR rf coil 1020. The sensitive window of the NMR rf coil 1020 was substantially 4 inches wide and located in the middle of the magnet. Therefore, the rf coil 1020 did not see the whole core sample in its entirety in one single measurement. The NMR data was acquired along the length of the whole core sample by manually moving the sample through the rf coil 1020 in one-inch steps for a total of 17 scans. In some implementations described later with reference to FIGS. 17-19, the sample can be automatically moved through the rf coil 1020 either in pre-defined steps, continuously, or both. One inch was chosen as a movement step to obtain the fluid content in the whole core sample at a resolution of 1 inch. To obtain the fluid content in the whole core sample at different resolutions, a movement step length equal to or less than the resolution can be chosen.

NMR Data Acquisition

The NMR signal was acquired using the CPMG pulse sequence. The echo time (TE) was 0.17 ms and each step consisted of four sets of 64 accumulations with an inter-scan delay of 500 ms.

Calibration Protocol and Response Map for NMR rf Coil 1020

In applications of magnetic resonance for spectroscopy, imaging, and logging, the rf coil generally serves two functions: (1) to excite the nuclear spins using the rf pulses from the coil; (2) to receive the signal when the excited nuclear spins induce current in the coil. For any given rf coil, both functions are spatial-dependent, and thus, heterogeneous in space. In this specification, a response map of a given rf coil is defined as the spatial distribution of the detected relative signal intensity at different positions of the rf coil. The definition accounts for both the spatial dependence on excitation and detection of the spin system by the rf coil.

A response map of an rf coil can be determined by two methods. The first is by calculation using Maxwell Equations. For any coils used in measurement or newly designed, such calculations are a classical electrodynamic problem that can yield accurate results. The approach itself has no limit on spatial resolution. The spatial resolution will be limited only by the measurement sensitivity to allow meaningful data processing. The second method is by mapping the response map by measurements using a standard sample with finite size. As described later, the standard sample is moved through the sensitive region of the coil to obtain the response map. The resolution of the response map is determined, and therefore, the spatial resolution of the final measurement is a function of the size of the standard sample. The ideal standard sample should be thin and have a large NMR signal. The best standard sample would approximate a Dirac delta function. The size of the standard sample must be selected equal to or 1/n (n is an integer) of the desired spatial resolution. As described later, in a one-dimensional application, the response map is a curve of a total of n data points $\{r_1, r_2, r_3, \ldots, r_n\}$, and the step (that is, distance) between each data point defines the spatial resolution l.

The calibration protocol is implemented because the detection sensitivity at the end of the NMR rf coil 1020 is not the same as the detection sensitivity at the middle of the NMR rf coil 1020. Therefore, the system 1000 implements the calibration protocol to determine an accurate mapping of the response curve of the NMR rf coil 1020 for accurate whole core sample logging. The calibration protocol was implemented with a standard sample described with reference to FIGS. 3A-3C.

FIG. 3A is a schematic diagram of a standard NMR sample 300. The standard NMR sample 300 has a diameter that is smaller than the inner diameter of the NMR rf coil 1020 and a thickness (or axial length) that is less than the axial length of the NMR rf coil 1020. In some implementations, the thickness of the standard NMR sample 300 can be substantially equal to the resolution at which the fluid content of the rock sample 1030 is to be determined. The standard NMR sample 300 can have a known fluid content. The fluid content can include water and other dopants, the concentrations of which are known. For example, the fluid content can be selected to shorten the $T_2$ time of the fluid. The standard NMR sample 300 can be disc-shaped or cylindrical to map the response curve of the NMR rf coil 1020 and to calibrate the fluid content in the whole core samples.

FIG. 3B shows a $T_2$ spectrum of fluid in the standard NMR sample of FIG. 3A. For certain example tests described, the inner diameter and thickness of the standard sample 300 were substantially 3.68 inches and 1.0 inches, respectively. The standard NMR sample 300 was filled with substantially 178.2 grams (g) or 178.2 milliliters (mL) of double-distilled water doped with copper sulfate ($CuSO_4$) with a concentration of substantially 215 parts per million (ppm) to shorten the $T_2$ to 70 ms as shown in plot 302 of FIG. 3B.

To obtain the response map of the NMR rf coil 1020, the standard NMR sample 300 is placed into the NMR rf coil 1020, and pushed through the NMR rf coil 1020 in steps, each equally spaced step being equal to or 1/n (n is an integer) of the resolution at which the fluid content in the rock sample 1030 is desired. FIG. 3C is a response map table of relative signal intensities at respective standard NMR sample positions. For certain example tests described, the NMR CPMG echo is acquired at one-inch step intervals. Because the standard NMR sample 300 is substantially one-inch thick and because the NMR rf coil 1020 is substantially four-inches long, there are six relative positions for the standard NMR sample 300 at which the relative signal intensities were measured. The multiple relative signal intensities obtained at relative standard NMR sample positions are shown in table 304 (FIG. 3C).

In addition to mapping the NMR rf coil 1020 response curve, the standard NMR sample 300 also serves to calibrate the fluid content in the whole core samples. The percent bulk volume (pbv) fluid content in the rock is calculated using Equation 1.

$$pbv = r \frac{M_0^{core}/V^{core}}{M_0^{w}/V^{w}} \times 100\% \qquad (1)$$

In Equation 1, r is the response factor (or relative signal intensity) from Table 304, $M_0^{w}$ is the measured NMR signal for the standard NMR sample 300, $V^{w}$ is the measured NMR volume for the standard NMR sample 300, and $M_0^{core}$ is the measured NMR signal for the rock sample 1030, and $V^{core}$ is the measured NMR volume for the rock sample 1030.

Data Acquisition Protocol for Whole Core Samples

FIG. 4A is a schematic diagram of NMR data acquisition for a rock sample using the NMR test system, for example, the NMR test system 1000. To begin data acquisition, the end of a rock sample 1030 is positioned at the end of the NMR rf coil 1020, and NMR data is collected. Because of the end effects at the NMR rf coil 1020, the acquired data will be a noise signal. The end of rock sample 1030 is then moved into the NMR rf coil 1020 by a step having a length equal to a desired resolution of the fluid content in the rock sample. The NMR data collection step is repeated. FIG. 4B is a plot 400 of signal intensity at different relative positions of the NMR rf coil 1020 when the entirety of the NMR rf coil 1020 surrounds the whole core sample 1030. When the sample end is right outside the NMR rf coil 1020, the NMR signal is small (nearly zero). When the sample end is closer to the center of the NMR rf coil 1020, the signal intensity is high (nearly one). The plot 400 indicates that the NMR rf coil 1020 has a sensitive region that lies near the center of the NMR rf coil 1020. The sensitivity of the NMR rf coil 1020 is the highest in the sensitive region. When the sample is extended through the NMR rf coil 1020, the measured NMR signal includes the contribution of the homogeneous region in the center and the two ends with attenuated response. In this manner, the entirety of the rock sample 1030 is moved through the NMR rf coil 1020 in step-wise movements until the other end of the rock sample 1030 is positioned at the other end of the NMR rf coil 1020. For certain example tests described, a 12-inch whole core sample was pushed through the substantially 4-in NMR rf coil in one-inch steps as described earlier resulting in 17 NMR signal acquisitions.

In some implementations, quality control and stability check of the NMR test system 1000 can be performed. To do so, for example, the NMR standard sample 300 can be placed at the center of the NMR rf coil 1020 and a NMR signal can be acquired periodically (for example, once a day). To ensure that the selected inter-scan delay (for example, 500 ms) is sufficient for the spin to re-establish equilibrium for successive scans, longer delays can be tested on randomly selected whole core samples to check for any observable signal enhancement. For certain example tests described, the quality control and stability checks were performed and no observable signal enhancements were found.

Data Inversion

The computer system 1000 can implement data inversion by executing computer instructions encoded on one or more computer-readable storage media (for example, computer-readable memory) using one or more processors. In some implementations, the acquired NMR signal s(t) can be expressed using Equation 2.

$$s(t) = \int_0^\infty M_0(T_2) \exp(-t/T_2) dT_2 \qquad (2)$$

In Equation 2, $M_0(T_2)$ is the distribution of magnetization (also called transverse relaxation time spectrum), and t is time. The transverse relaxation time spectrum can be obtained with an inverse Laplace transform shown in Equation 3.

$$M_0(T_2) = L^{-1}\{s(t)\} = \frac{1}{2\pi i}\int s(t)\exp(t/T_2)dt \quad (3)$$

The acquired data s(t) is not continuous and always contains noise which can be expressed using Equation 4.

$$s(t_j) = \Sigma_i M_0^i(T_2^i)\exp(-t_j/T_2^i) + \delta(t_j) \quad (4)$$

In Equation 4, $\delta(t_j)$ represents the measurement errors, which, in this case, is noise. Obtaining $M_0^i(T_2^i)$ from Equation 4 is a classic inversion problem in NMR logging data processing. For certain example tests described, an algorithm called CONTIN was implemented using Matlab® software program (registered to Mathworks, Inc., Massachusetts, USA) to determine $M_0^i(T_2^i)$. The computer system 1002 implemented the algorithm to find a least square solution or a set (m number) of $M_0^k(T_2^k)$ to satisfy Equation 5.

$$\text{var} = \Sigma_{j=1}^n w_j[s(t_j) - \Sigma_{k=1}^m M_0^k \exp(-t_j/T_2^k)]^2 \quad (5)$$

The term var is the variable which is minimized (in other words, the least square solution).

In Equation 5, n is the number of acquired data points, $w_j$ are optional weighting factors that can be assigned, and m is the number of variables. To determine the least square solution, a pre-defined set of $T_2^k$ is used. Therefore, the exponential term in Equation 5 can be replaced with x variables defined as shown in Equation 6.

$$x_k(t_j) = \exp(-t_j/T_2^k) \quad (6)$$

With the replacement, Equation 5 becomes a set of linearized equations as shown in Equation 7.

$$\text{var} = \Sigma_{j=1}^n w_j[s(t_j) - \Sigma_{k=1}^m M_0^k x_k(t_j)]^2 \quad (7)$$

As described later, the computer system 1002 can implement NMR inversion as a classic linear least squares problem. In some implementations, the computer system 1002 can use regularized linear least squares method, as shown in Equation 8 to implement the NMR inversion.

$$\text{var} = \Sigma_{j=1}^n w_j[s(t_j) - \Sigma_{k=1}^m M_0^k x_k(t_j)]^2 + \alpha^2 \Sigma_{j=1}^n [\Sigma_{k=1}^m x_k(t_j)]^2 \quad (8)$$

The second term in Equation 8 is called the regularizer, and has a strength that is determined by regularization parameter $\alpha$.

The least squares fitting method can result in many different solutions for the same tolerance in the minimum variance represented by Equation 8. The issue of obtaining many different solutions can be addressed by incorporating complex constraints. For certain example tests described, the constraints represented by Equations 9.1 and 9.2 were used.

$$M_0^k(T_2^M) \geq 0 \quad (9.1)$$

$$M_0^1(T_2^1) = M_0^M(T_2^M) = 0 \quad (9.2)$$

Figures 5A, 5B:
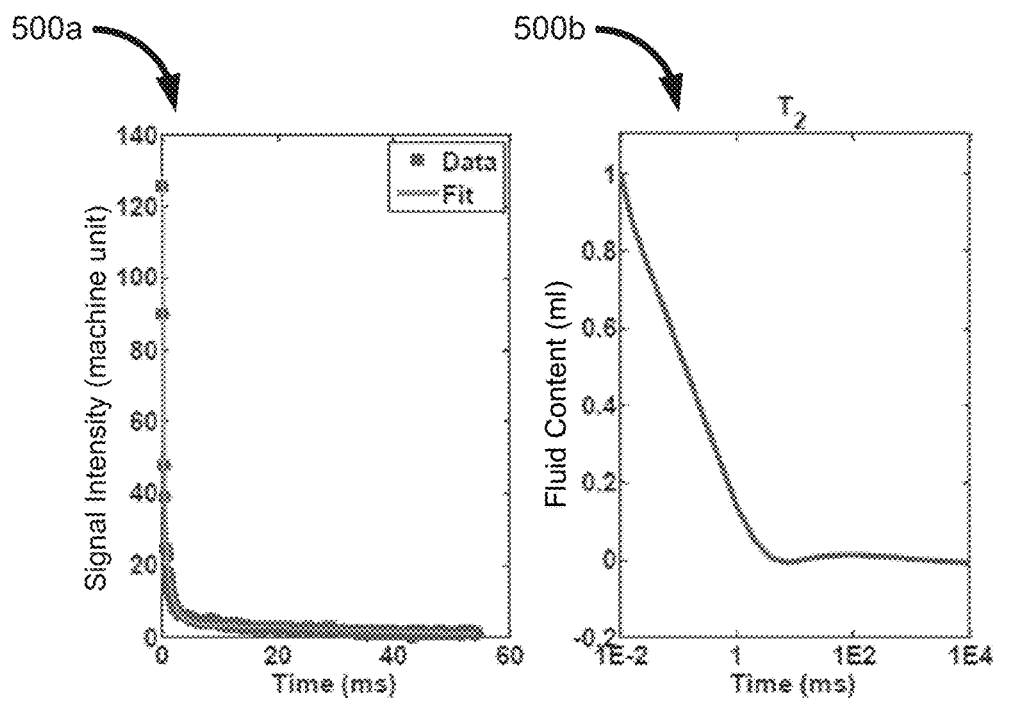
FIGS. 5A and 5B show inverted $T_2$ spectrum without constraints.
Figures 5C, 5D:
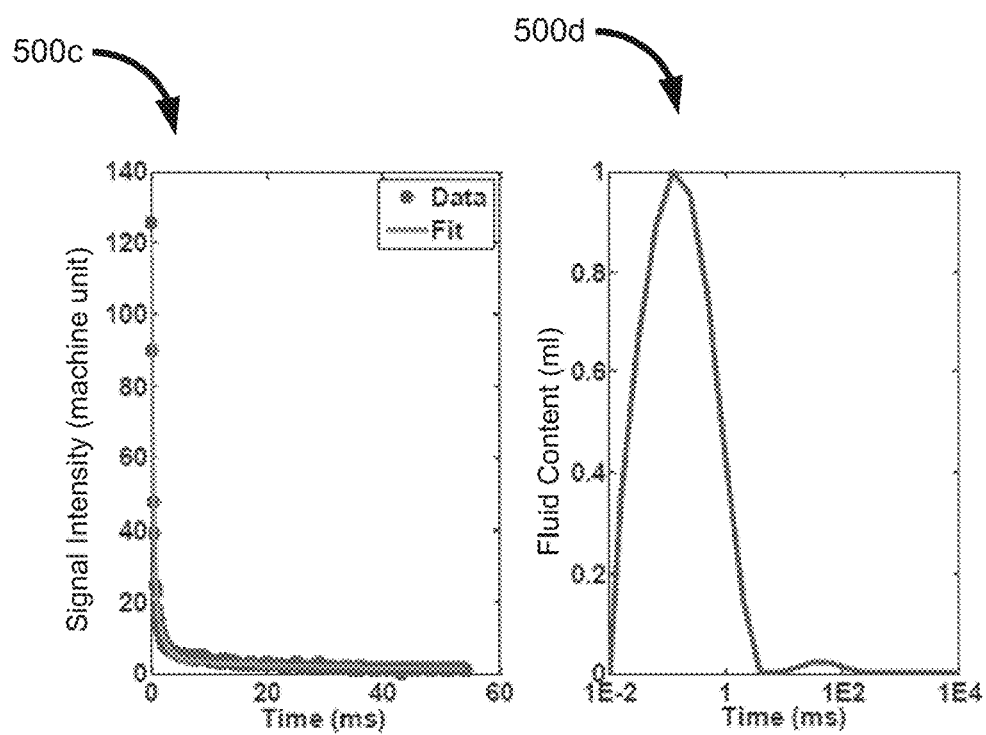
FIGS. 5C and 5D show inverted $T_2$ spectrum with constraints.

FIGS. 5A and 5B show inverted $T_2$ spectrum without constraints. FIGS. 5C and 5D show inverted $T_2$ spectrum with constraints. In plots 500a and 500c shown in FIGS. 5A and 5C, respectively, the lines represent calculated fits and the dots represent data. In plots 500b and 500d shown in FIGS. 5B and 5D, respectively, the lines represent the data used for fitting. The calculation error tolerance was set the same for both inversions, that is, the inversion with constraints and the one without. Both spectra reflect possible real $T_2$ distribution.

Noise Truncation

When NMR CPMG echo data is acquired, generally more echoes are measured to ensure no useful data is neglected. As a result, a significant number of data points at the end of the acquired echo train may be mainly noise without any useful information. Including these data points can consume significant extra computational time and can lead to inaccurate inversion and results, since they are treated as real information. Therefore, truncating detailed noise from the acquired CPMG echoes before the inversion can be useful.

In some implementations, a piecewise linear fitting method can be used to identify if the acquired data was noise. Specifically, the echo data can be split into N equal width windows, and the slope of the data $s_i$ (for i=1, ..., N) from the first to the N-th window is calculated using linear fitting in each window. A slope threshold $s_{th}$ can then be set. If starting from the n-th point, all the remaining slopes would be smaller than this threshold, that is, $s_i < s_{th}$ for i=n, ..., N. All the data points from windows n to N can then be considered as noise. Only the data from windows 1 to n−1 can be used for inversion. For certain example tests described, N=100 and $s_{th} = \exp(-4.5)$ were chosen.

Figure 6B:
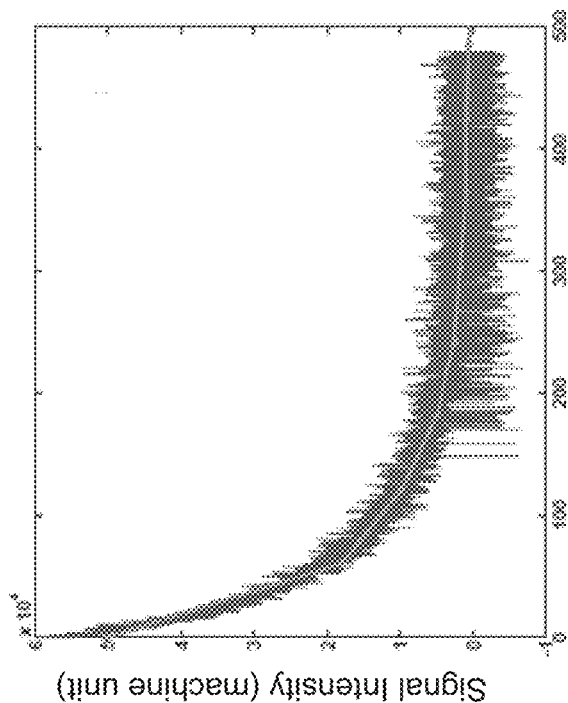
FIGS. 6A and 6B show illustrations of noise truncation.
Figure 6A:
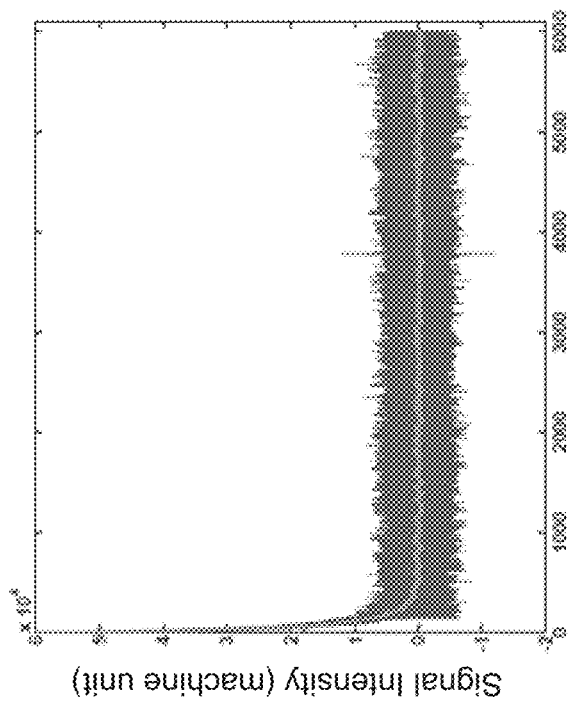

FIGS. 6A and 6B show illustrations of noise truncation. Plot 600a shows the total CPMG echoes with long noise tail. Plot 600b shows the total CPMG echoes with truncated signal according to the protocol described earlier. To develop plot 600a, 56,604 data points were taken and a linear fit for all the data was obtained over a repeated window. To develop plot 600b, 4,528 data points were taken and data was retained with decay rate greater than exp(−4.5) in set window. The lines show the linear fit in each plot.

An inversion program with the features described earlier was then developed. A test run on synthetic data was performed using the computer system 1002. The synthetic data was calculated using $S(t) = \exp(-t/1.5) + \exp(-t/10) + \exp(-t/150) + \text{noise}$. FIGS. 7A and 7B show results of an inversion test on the synthetic data with the signal to noise ratio (SNR) set to substantially 18. FIGS. 7C and 7D show results of an inversion test on the synthetic data with the SNR set to substantially 7. In plots 700a and 700c shown in FIGS. 7A and 7C, respectively, the lines are the calculated signals from the inverted spectras. Plots 700b and 700d in FIGS. 7B and 7D, respectively, show the inverted $T_2$ spectra at different signal-to-noise ratios, showing better inverted results at larger signal-to-noise ratios.

Deconvolution

The data inversion described earlier uses the $T_2$ spectra of each NMR measurement in the NMR rf coil 1020. From the measurement of the response map (shown in Table 304 of FIG. 3C), it can be seen that these spectra and the resulting fluid content (in pbv) are an average for 5 inches of core, except at the two ends of the core where NMR echoes were measured when the sample was only partially inside the NMR rf coil 1020. In particular, the diameter of the NMR rf coil 1020 is 4 inches. The sensitive region of the NMR rf coil, which obtains signal from 5 inches of sample along the longitudinal axis, is 5 inches. The computer system 1002 can implement the deconvolution techniques described later to obtain fluid contents at a resolution equal to a length of each step at which the rock sample 1030 was moved inside the NMR rf coil 1020 to obtain the NMR signal.

FIG. 8 is a schematic illustration of a rock sample moving into a NMR rf coil and corresponding detected signals. The effective response window, that is, the portion of the NMR rf coil 1020 that is sensitive to the fluid content in the sample, excludes the ends of the coil 1020. For example, as shown in table 304 in FIG. 3C, the effective response window for a 4-inch NMR rf coil is 5 inches, that is, between the $1^{st}$ relative position and the $5^{th}$ relative position. Consequently, a detected signal when the core extends across the NMR rf coil 1020 can be expressed as shown in Equation 10.

$$S_n = r_1\alpha_n + r_2\alpha_{n-1} + r_3\alpha_{n-2} + r_4\alpha_{n-3} + r_5\alpha_{n-4} \quad (10)$$

In Equation 10, r represents the relative signal intensities measured in the effective response window of the NMR rf coil 1020. In general, the number of r values equals the length of the effective response window of the NMR rf coil 1020. For example, for the NMR rf coil described with reference to FIG. 3C, there are 5 values of r ($r_1=0.35$, $r_2=1.00$, $r_3=0.98$, $r_4=0.98$, and $r_5=0.49$; from table 304 of FIG. 3C). S is the detected NMR signal and $\alpha_i$ (for i=1, 2, ..., k, where k corresponds to the total length of the whole core sample in inches because the resolution for this example is 1 inch) represents the bulk fluid at the i-th inch. FIG. 8 can be translated into Equation 11 in matrix form.

$$\begin{bmatrix} s_1 \\ s_2 \\ \vdots \\ s_{k+4} \end{bmatrix} = \begin{bmatrix} r_1 & & & & & \\ r_2 & r_1 & & & & \\ r_3 & r_2 & r_1 & & & \\ & & \ddots & & & \\ & r_5 & r_4 & r_3 & r_2 & r_1 \\ & & & & \ddots & \\ & & & r_5 & r_4 & r_3 \\ & & & & r_5 & r_4 \\ & & & & & r_5 \end{bmatrix} \times \begin{bmatrix} a_1 \\ a_2 \\ \vdots \\ a_k \end{bmatrix} \quad (11)$$

The detected NMR signal S is represented in Equation 11 as shown in Equation 12.1.

$$S = \begin{bmatrix} s_1 \\ s_2 \\ \vdots \\ s_{k+4} \end{bmatrix} \quad (12.1)$$

The matrix of relative signal intensity values is represented by R as shown in Equation 12.2.

$$R = \begin{bmatrix} r_1 & & & & & \\ r_2 & r_1 & & & & \\ r_3 & r_2 & r_1 & & & \\ & & \ddots & & & \\ & r_5 & r_4 & r_3 & r_2 & r_1 \\ & & & & \ddots & \\ & & & r_5 & r_4 & r_3 \\ & & & & r_5 & r_4 \\ & & & & & r_5 \end{bmatrix} \quad (12.2)$$

The matrix of core length distances is represented by A as shown in Equation 12.3.

$$A = \begin{bmatrix} a_1 \\ a_2 \\ \vdots \\ a_k \end{bmatrix} \quad (12.3)$$

In Equations 12.1, 12.2, and 12.3, the dimensions of S, R, and A are (k+4)×1, (k+4)×k, and k×1, respectively. This represents an over-determined problem because the dimension of S is larger than that of A. Using the definitions in Equations 12.1, 12.2 and 12.3, Equation 11 can be written in matrix form as shown in Equation 13.

$$S = RA \quad (13)$$

Equation 12 can be converted to Equation 14.

$$R^T S = R^T R A \quad (14)$$

In Equation 14, R' is the transpose of matrix R. In Equation 14, R'R is a k×k matrix and R'S is a k×1 matrix. Equation 15 can be used to determine A.

$$A = (R^T R)^{-1} R^T S \quad (15)$$

In Equation 15, $(R^T R)^{-1}$ is the inverse of $R^T R$. Matrix A is the fluid content (in pbv) in the core at one-inch resolution.

Regularization

In some implementations, the determination of $(R^T R)^{-1}$ can result in errors. To avoid or overcome the errors, a general linear least squares technique, such as that described earlier with reference to Equation 8, can be implemented. Alternatively, or in addition, a more definite singular-value decomposition technique can be implemented where all the whole core samples have the same matrix R. In some implementations, the computer system 1002 can perform singular value decomposition of matrix R'R as shown in Equation 16.

$$R^T R = U \Sigma V^T \quad (16)$$

In Equation 16, $V^T$ denotes the conjugate transpose of V. U and V are unitary matrices, each of which satisfies $U^T U = V^T V = 1$ (where 1 signifies an identity matrix). Also, $\Sigma$ is a diagonal matrix represented by Equation 17.

$$\Sigma = \begin{bmatrix} \sigma_1 & & & 0 \\ & \sigma_2 & & \\ & & \ddots & \\ 0 & & & \sigma_k \end{bmatrix} \quad (17)$$

Using Equation 16, Equation 15 can be re-written as Equation 18.

$$A = (U \Sigma V^T)^{-1} R^T S = (V^T)^{-1} \Sigma^{-1} U^{-1} R^T S \quad (18)$$

Using the property of unitary matrix U and V, Equation 18 can be re-written as Equation 19.

$$A = V \Sigma^{-1} U^T R^T S \quad (19)$$

In Equation 19, $\Sigma^{-1}$ is represented as Equation 20.

$$\Sigma^{-1} = \begin{bmatrix} s_1^{-1} & & & 0 \\ & s_2^{-1} & & \\ & & \ddots & \\ 0 & & & s_k^{-1} \end{bmatrix} \quad (20)$$

Figure 9:
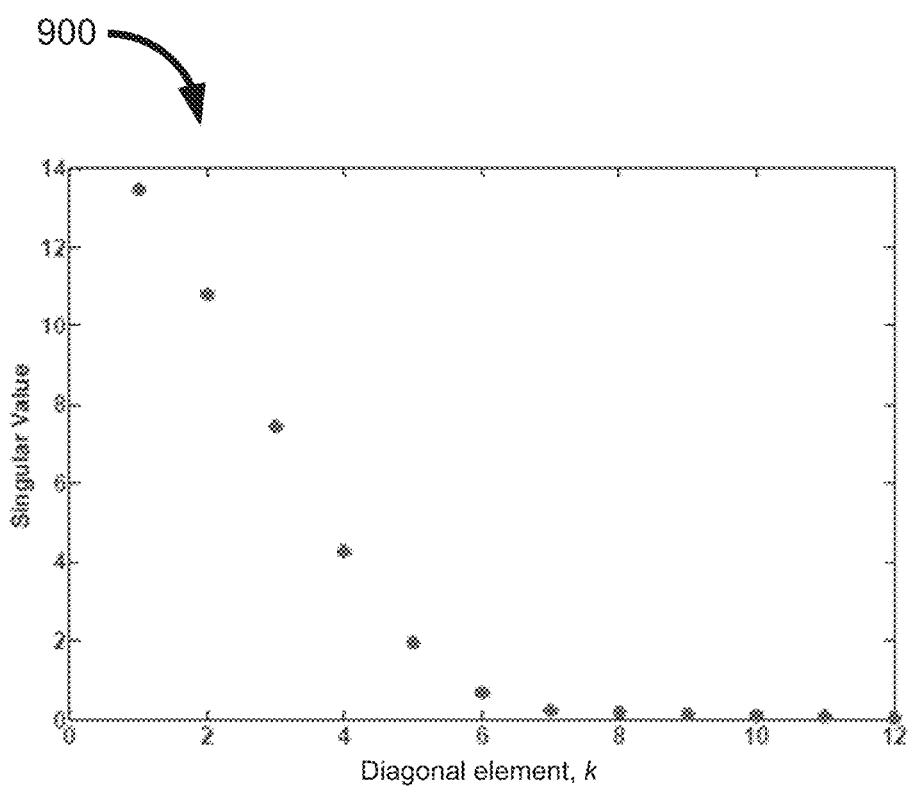
FIG. 9 is a plot of a diagonal matrix of singular values used to determine the fluid content of whole core samples.

Matrix R in Equation 12.2 can be written for a given k. For different k values, matrix R in Equation 12.2 and the corresponding calculations and results are different. For certain example tests described, the whole core samples were 12 inches long; so, k=12. For slightly longer whole core samples, k=13. Assuming that k=12, $\Sigma^{-1}$ from Equation 20 can be determined. FIG. 9 is a plot 900 of diagonal elements in $\Sigma$. As shown in plot 900, a few elements have values close to zero and will add significant errors to the final results if Equation 20 was used to calculate $\Sigma^{-1}$. Instead, a threshold $\sigma_{th}$ was defined for the diagonal elements in matrix $\Sigma$, and for any element less than the threshold (that is, $\sigma_i < \sigma_{th}$), the corresponding $\zeta_i^{-1}$ is set to be equal to 0 resulting in $\Sigma^{-1}$ being determined using Equation 21.

$$\sum\nolimits^{-1} = \begin{bmatrix} \zeta_1^{-1} & & & 0 \\ & \ddots & & \\ & & \zeta_{th}^{-1} & \\ & & & \ddots \\ 0 & & & 0 \end{bmatrix} \quad (21)$$

Implementing the regularization techniques described does not sacrifice a significant portion of accuracy because the majority information in matrix $\Sigma$ carries little information as long as the threshold $\zeta_{th}$ is not too large. For certain example tests described, where k=12, the threshold was chosen such that the last six diagonal elements in matrix $\Sigma^{-1}$ were zero.

Deconvolution by Convex Optimization

The solution matrix A (shown in Equation 13) can also be determined by posing the deconvolution as a convex optimization problem. Equation 22 poses an unconstrained objective function z in Lagrangian form:

$$\operatorname{argmin}_A z = \|RA-S\|_2^2 + \alpha TV(A) + \beta \|\phi(A)\|_1 \quad (22)$$

where TV (A) is the total variation of A, $\phi$ is a function that transforms A into a wavelet domain, $\alpha$ is a regularization parameter (constant) which determines the penalty (that is, weight or coefficient) of the total variation of A, and $\beta$ is a parameter (constant) which determines the penalty of the wavelet domain transform of A. Enclosing a term or equation within a pair of double vertical lines ($\| \ldots \|$) signifies a norm. $\| \ldots \|_1$ is the $l_1$ norm, which is the sum of the absolute values of all components. $\| \ldots \|_2$ is the Euclidian norm, which is the square root of the sum of squares of all components. For example, for a vector x=[2, 9, 5], $\|x\|_1$=2+9+5=16, and $\|x\|_2 = \sqrt{2^2+9^2+5^2} \approx 10.5$.

Solution A which minimizes the objective function in Equation 22 can be found by determining where the following gradient equation 23 equals zero:

$$\Delta z \approx 2A'(RA-S) + \sqrt{\left[\alpha_t \frac{\partial A}{\partial t}\right]^2 + \left[\alpha_x \frac{\partial A}{\partial x}\right]^2} + \beta \phi' W \phi A \quad (23)$$

where $\alpha_t$ is a sub-regularization parameter for $\alpha$ (from Equation 22) along the time dimension, $\alpha_x$ is a sub-regularization parameter for $\alpha$ (from Equation 22) along the distance dimension, and W is a diagonal weight matrix. The symbol $\nabla$ denotes gradient; therefore, $\nabla z$ is the gradient of z.

Figure 10B:
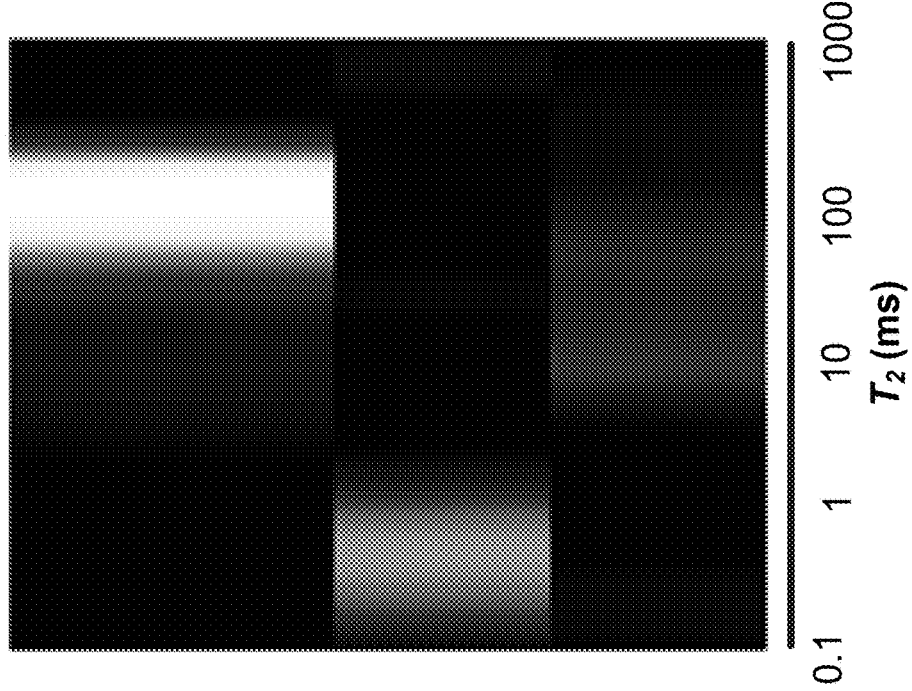
FIG. 10B shows a deconvoluted signal of the composite rock sample in FIG. 10A.
Figure 10A:
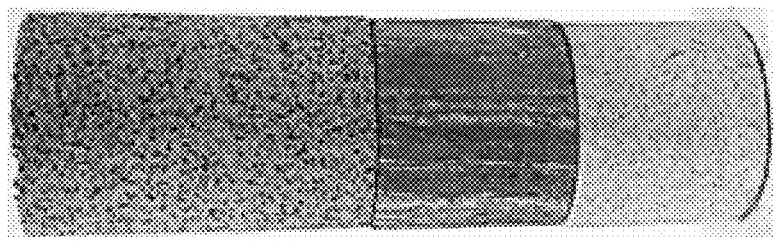
FIG. 10A shows a composite rock sample.

FIG. 10A shows a composite rock sample, which was prepared by stacking three 1-inch diameter plugs. The composite rock sample was saturated with 2 weight % potassium chloride (KCl) solution. The top section of Berea sandstone was 1.5 inches in length, the middle section of Mancos shale outcrop was 1 inch in length, and the bottom section of tight sandstone was 1 inch in length. FIG. 10B shows the deconvoluted signal, utilizing the method of convex optimization described previously. The signals were acquired with 0.25-inch spatial resolution utilizing a 4-inch long NMR rf coil.

Obtain Echo by Echo Trains

The techniques described earlier can be expanded to obtain the full CPMG echo train which contains additional information. Each acquired CPMG echo train contains m number of echoes and can be used as the input. In Equation 13 earlier, S and A were vectors. In the implementation to obtain echo trains, S and A are matrixes. The signal, S, becomes Equation 24.

$$S = \begin{bmatrix} s_{1,1} & \cdots & s_{1,m} \\ \vdots & \ddots & \vdots \\ s_{k+n-1,1} & \cdots & s_{k+n-1,m} \end{bmatrix} \quad (24)$$

Each row in the matrix S of Equation 24 is a measured echo train. The fluid content, A, becomes Equation 25.

$$A = \begin{bmatrix} a_{1,1} & \cdots & a_{1,m} \\ \vdots & \ddots & \vdots \\ a_{k,1} & \cdots & a_{k,m} \end{bmatrix} \quad (25)$$

Each row in the matrix A of Equation 25 represents the echo train that is desired with higher spatial resolution and without the coil end effects. The matrix R in Equation 12.2, which represents the response map of the rf coil, remains the same as defined earlier, and can be solved as explained earlier.

Signal Optimization and Noise Suppression

NMR measurements sometimes include a variety of noise types which contaminate the true representative signal of fluid contents. The basic noise types include background ambient noises, NMR instrument noises, and specific noises associated with NMR response to each rock formation. To obtain fluid content and echo by echo trains using the techniques described earlier, the post-processing techniques can be optimized to suppress the noise. In the following paragraphs, examples of noise suppression techniques are disclosed. The techniques can be implemented as computer instructions stored on a computer-readable medium and executable by one or more processors, for example, of the computer system 1002.

Matched Filter Denoising Methods

To implement this method, a number of measurements are taken inside a uniform (preferably lengthy) formation to improve filter accuracy. The matched filter can be implemented as a minimization problem between neighboring measurements, as represented by Equation 26.

$$J(f) = \frac{1}{2} \left\| \begin{bmatrix} S_i \\ S_{i+1} \\ \vdots \\ S_{i+n-1} \end{bmatrix} f - \begin{bmatrix} S_{i+1} \\ S_{i+2} \\ \vdots \\ S_{i+n} \end{bmatrix} \right\|_2^2 + \lambda \|Gf\|_2^2 \qquad (26)$$

In Equation 26, $S_i$ is the i-th measurement inside a uniform formation, $S_{i+n}$ is the last measurement used to compute the matched filter f, and G is a Gaussian smoothing function center at the middle point of all measurements. To mitigate the edge effects for the filter, the Gaussian smoothing function can be written as shown in Equation 27.

$$G(r) = \frac{1}{R\sqrt{2\pi}} e^{-\frac{r^2}{2R^2}} \qquad (27)$$

In Equation 27, R is the measurement length used for filter calculation, and r is the offset between each measurement to the midpoints. G(r) is the output Gaussian weight, and $\lambda$ is the constraint weight for the Gaussian smoothing function. The solution for the matched filter can be expressed as shown in Equation 28.

$$f = (S_{i-1}{}^T S_{i-1} + \lambda G^T G)^{-1} S_{i-1}{}^T S_i \qquad (28)$$

The matched filter f solution benefits from a large amount of sampling that is restricted to formation composition.

In some implementations, the computer system 1002 implements the following workflow for matched filter denoising. The computer system 1002 reads all the NMR measurements and sorts the measurements to a common formation data bin. In a first branch, the computer system 1002 searches for the formation with the most measurements. The computer system 1002 designs the cost function for matched filter to minimize the $l^2$-norm of neighboring measurements. The $l^2$-norm is a vector norm, which is sometimes called the magnitude of a vector. The computer system 1002 designs and applies a Gaussian weight function to mitigate edge effects. The computer system 1002 iteratively solves for the matched filter until data residues converge to error tolerance. In a parallel, second branch, the computer system 1002 re-sorts NMR measurements back to original order. The computer system 1002 then applies the obtained matched filter for all measurements and outputs filtered NMR data.

Wiener Filter Denoising Method

To implement this method, the computer system 1002 can use samples of noise outside the formation, which subsequently reduces the previous constraint. The computer system 1002 can implement this method using fewer NMR measurements outside the formation. The sampled data can be characterized as noise. The wiener filter can be expressed in frequency domain as shown in Equation 29.

$$f(\omega) = (|G(\omega)|^2 |S^*(\omega)S(\omega) + N^*(\omega)N(\omega))^{-1} \times G^*(\omega)S^*(\omega) S(\omega) \qquad (29)$$

In Equation 29, $N(\omega)$ is the noise representation in frequency domain after a Fourier transform. Correspondingly, $S^*(\omega)$ and $G^*(\omega)$ represent the complex conjugate of NMR measurements and Gaussian smoothing function in frequency domain, respectively. The wiener filter denoising method depends on the accuracy of outside noise measurement and can become unstable in field applications.

In some implementations, the computer system 1002 implements the following workflow for wiener filter denoising method. The computer system 1002 reads all NMR measurements. The computer system 1002 samples a number of measurements outside of the formations, treated as background noise. The computer system 1002 implements a Fourier transform of all measurements to frequency domain. The computer system 1002 directly solves wiener filter in frequency domain. The computer system 1002 applies wiener filter to all measurements. The computer system 1002 converts data back to time domain and outputs the filtered data.

Results

Implementing the techniques described earlier on rock samples (for example, whole core samples) can yield the following results: CPMG echoes at intervals equal to the length of the NMR rf coil, $T_2$ spectrum at intervals equal to the length of the NMR rf coil, $T_2$ spectrum for the entire rock sample, fluid content at a resolution equal to the length of the NMR rf coil, fluid content at a resolution equal to a length of a step by which the rock sample was moved within the NMR rf coil, and average fluid content over the entire length of the rock sample.

Figures 11A, 11B:
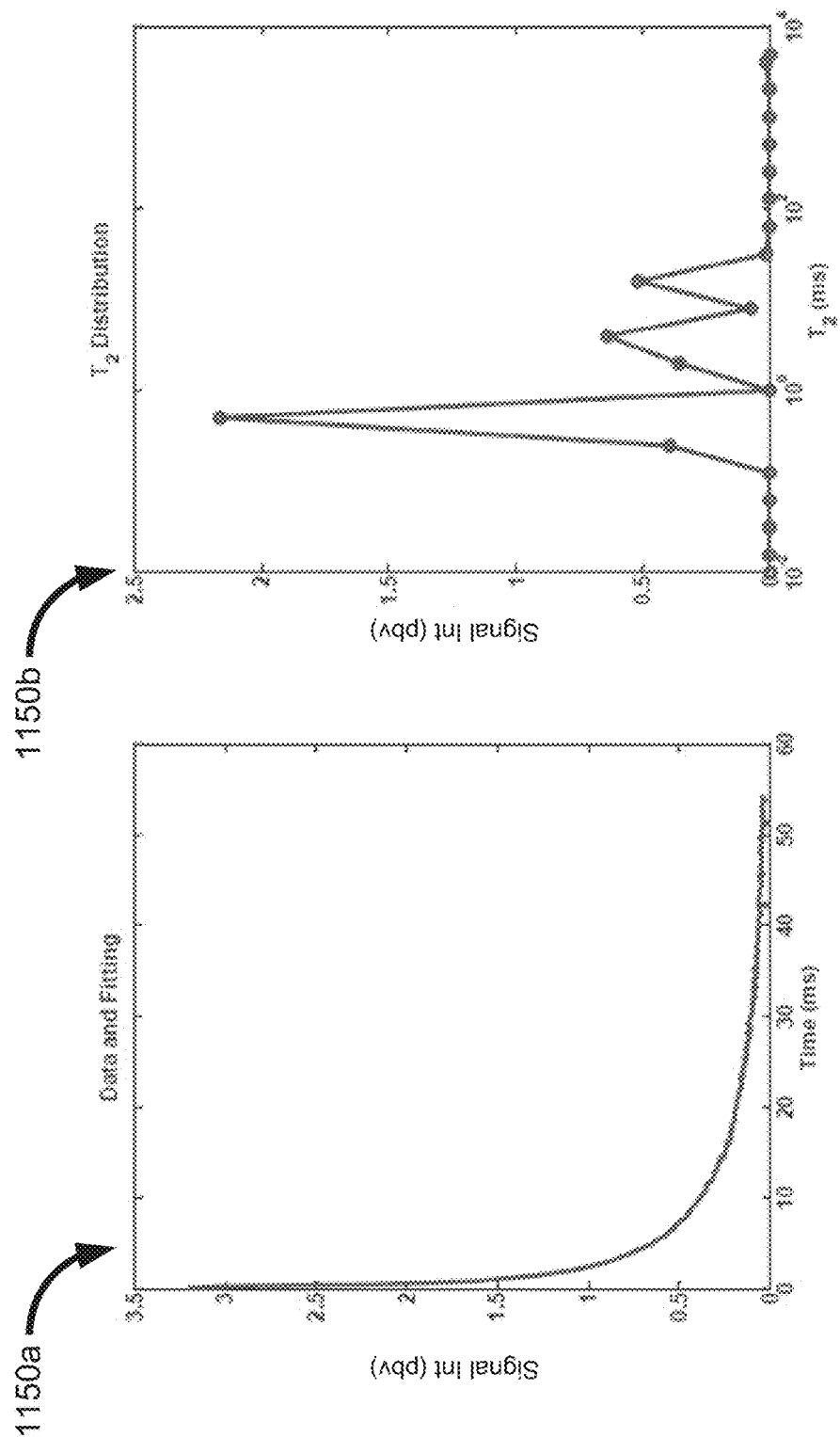
FIGS. 11A and 11B show the acquired CPMG echo over a four-inch section on a whole core sample and its inverted $T_2$ spectrum.
Figure 12:
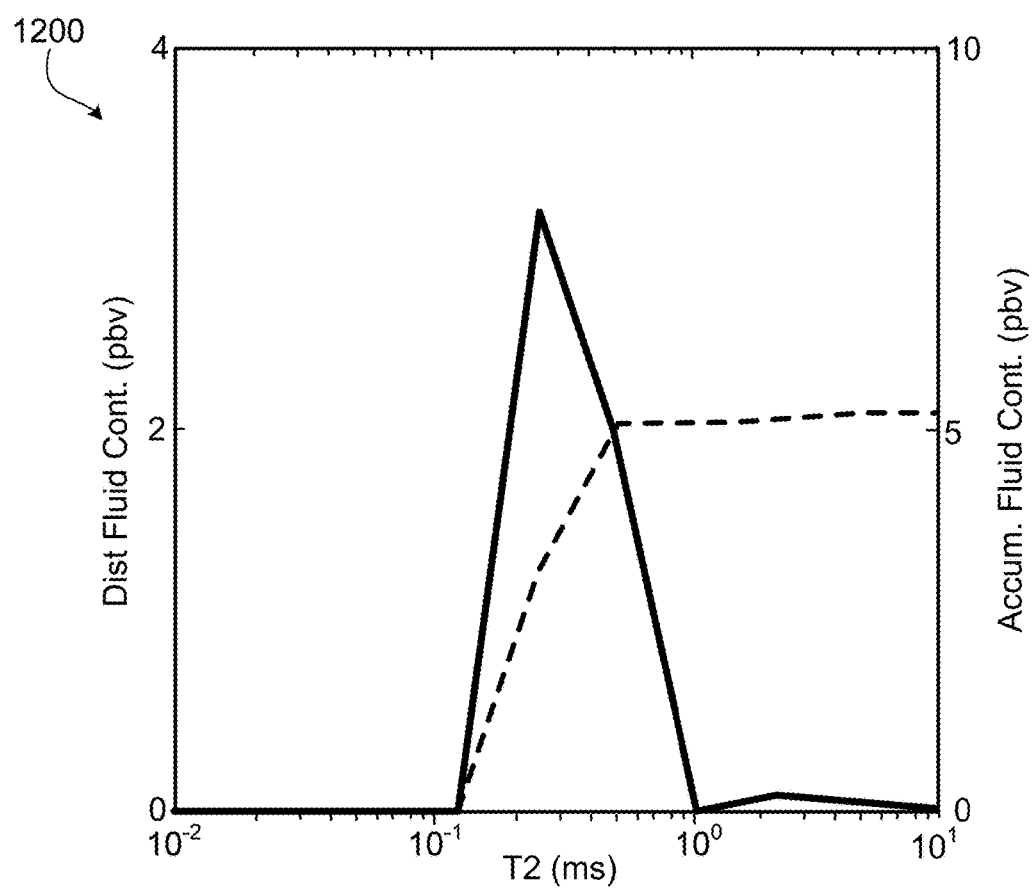
FIG. 12 is an example plot of distributive and accumulative $T_2$ spectra averaged over a length of a whole core sample.
Figure 13:
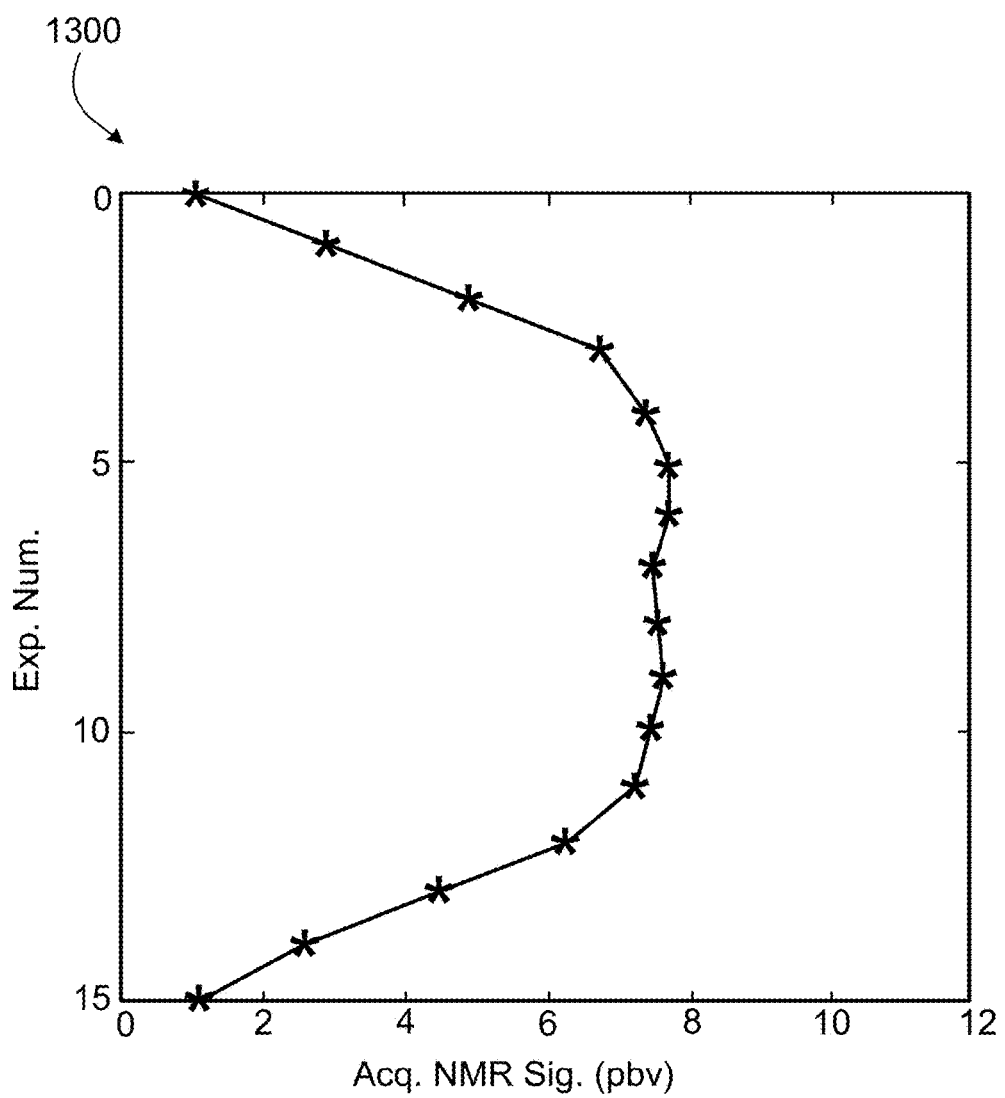
FIG. 13 is an example plot of fluid content in percent bulk volume averaged over the length of the NMR rf coil.
Figure 14:
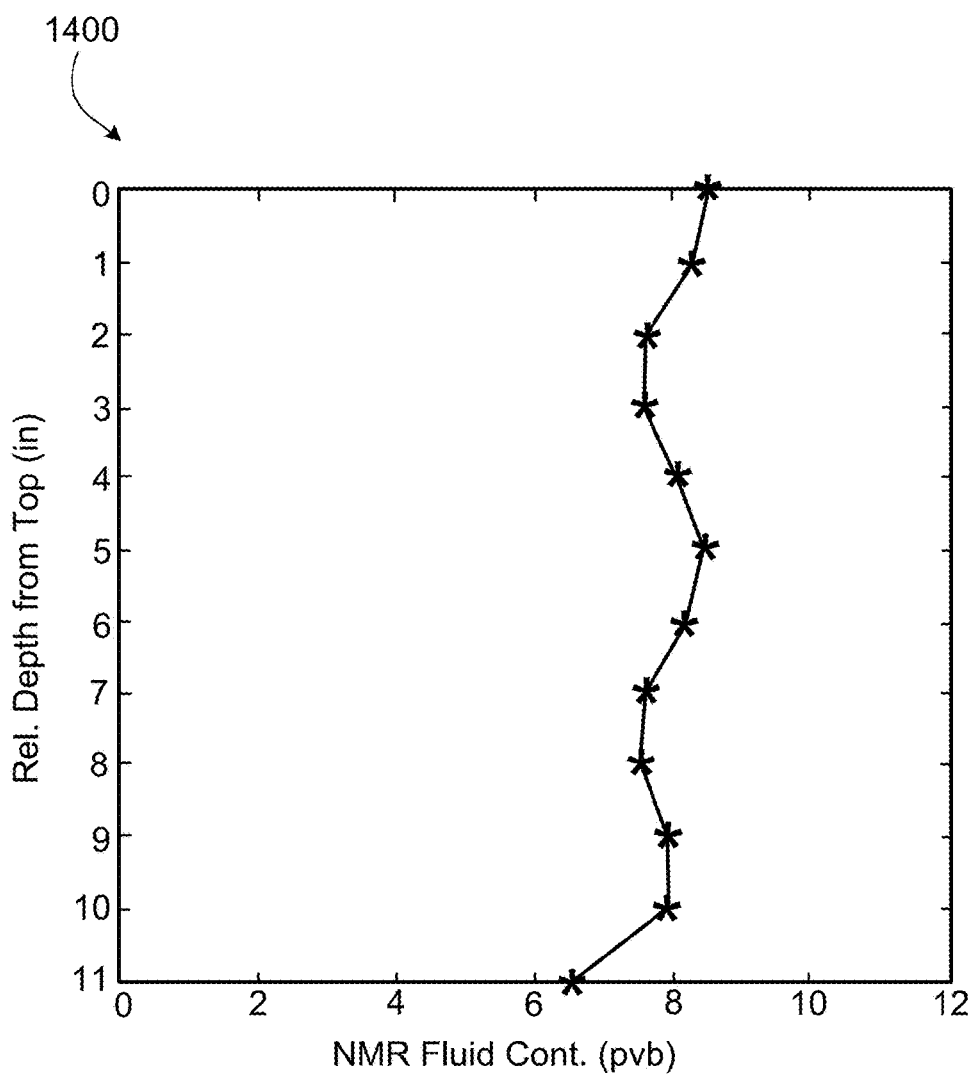
FIG. 14 is an example NMR log of full core at a resolution equal to a length of a step by which the whole core sample is moved within the NMR rf coil.
Figure 15A:
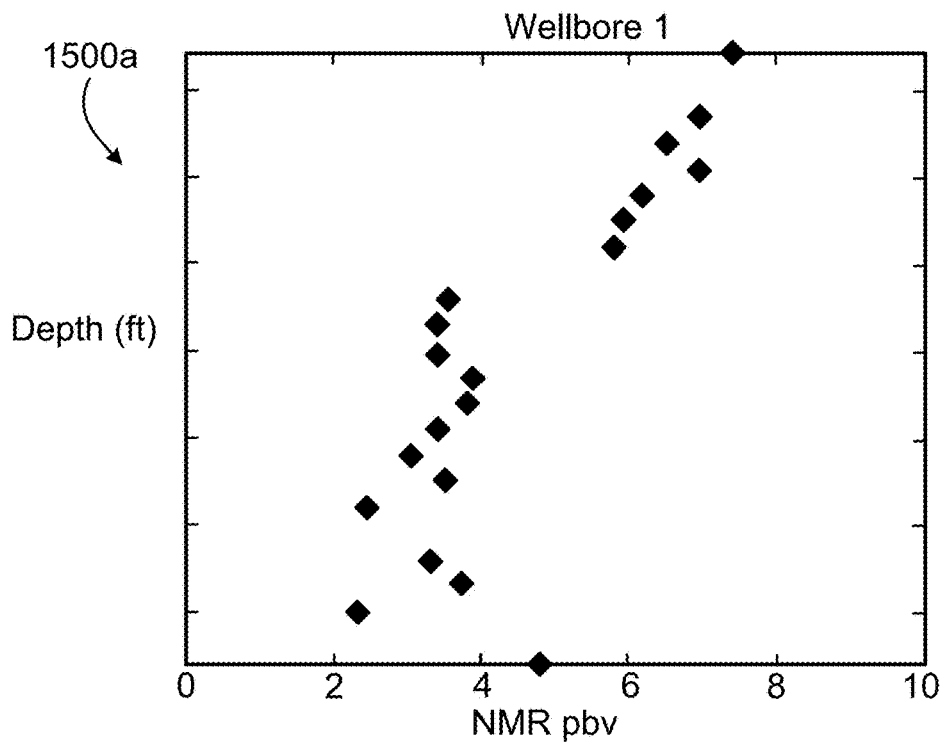
FIGS. 15A and 15B show averaged fluid content of whole core samples retrieved from different depths in two different wellbores.
Figure 15B:
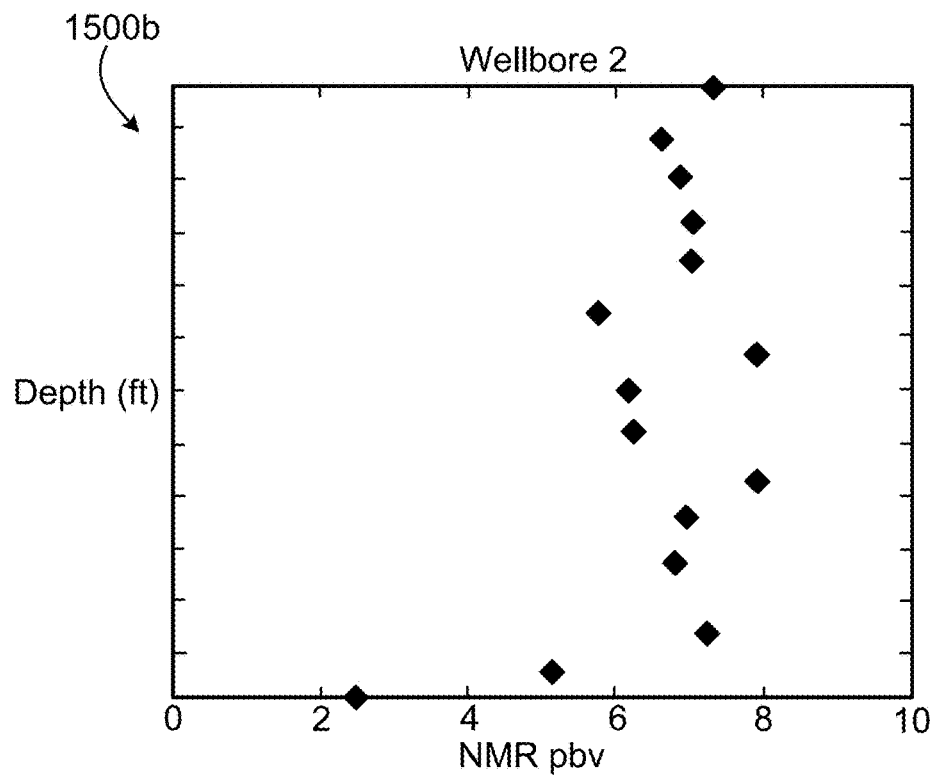

The results obtained for certain example tests described are shown with reference to FIGS. 11A, 11B, 12, 13, 14, 15A, and 15B. FIGS. 11A and 11B show the acquired CPMG echo over a four-inch section on a whole core sample (plot 1150a) and its inverted $T_2$ spectrum (plot 1150b). The SNR of the acquired NMR signal is more than 200. The $T_2$ distribution reflects a combined effect of pore size and fluid property. The $T_2$ spectrum in FIG. 11B implies that in the 4-inch section of the whole core sample, some fractures are likely to be present. FIG. 12 shows an example plot 1200 of distributive and accumulative $T_2$ spectra averaged over a length of a whole core sample. In plot 1200, the solid line shows the distributive $T_2$ spectrum averaged over the length (substantially 12 inches) of a whole core sample, and the dashed line shows the accumulative $T_2$ spectrum averaged over the length of the whole core sample. FIG. 13 is a plot 1300 of fluid content (in pbv) averaged over four inches (the length of the NMR rf coil). FIG. 14 is an example NMR log 1400 of the whole core sample at a resolution of one inch, which is equal to a length of a step by which the whole core sample was moved within the NMR rf coil. FIGS. 15A and 15B show averaged fluid content of whole core samples retrieved from different depths in two different wellbores. The plot 1500a shows the depth (in feet) in a first wellbore from which different whole core samples were obtained, and the fluid content (in pbv) of each sample. The plot 1500b shows the depth (in feet) in a second wellbore from which different whole core samples were obtained, and the fluid content (in pbv) of each sample. The plots can be used to distinguish zones in each wellbore based on fluid content.

Figure 16:
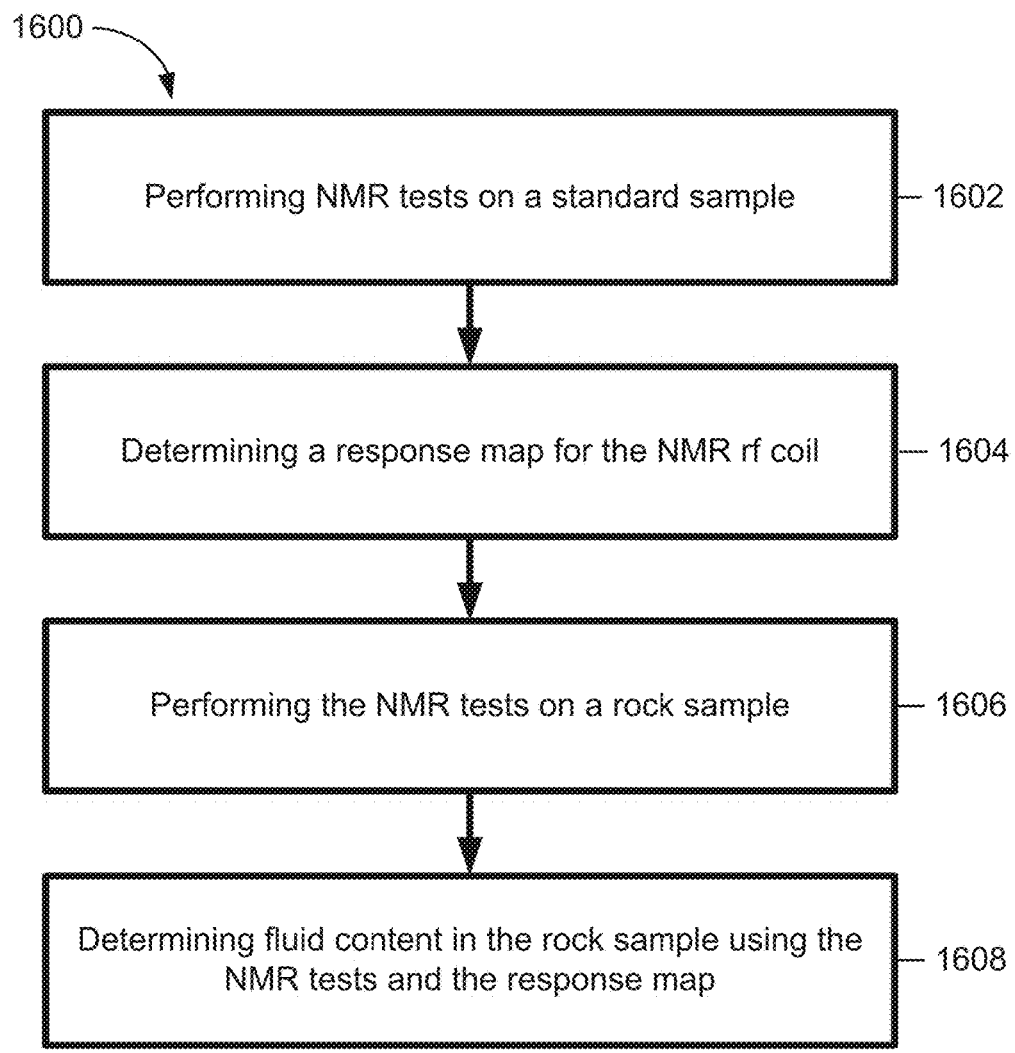
FIG. 16 is a flowchart of an example process for determining fluid content in a rock sample.

FIG. 16 is a flowchart of an example process 1600 for determining fluid content in a rock sample. The process 1600 can be implemented by the NMR test system 1000 described earlier with reference to FIG. 1. At 1602, NMR tests can be performed on a standard sample using an NMR rf coil having a length. At 1604, a response map for the NMR rf coil can be determined. At 1606, the NMR tests can be performed using the NMR rf coil on a rock sample containing fluid. The length of the rock sample is greater than that of the NMR rf coil. At 1608, fluid content in the rock sample can be determined using results of the NMR tests using the NMR rf coil on the rock sample and using the response map for the NMR rf coil.

For certain example tests described, the desired resolution of the core log was one inch. Accordingly, the rock sample was moved in one inch steps through the NMR rf coil. The desired resolution can be different from one inch. The thickness of the standard sample and the step-wise distance by which the standard sample is moved through the NMR rf coil can match the desired resolution.

Applications

As described earlier, the techniques described can be implemented to acquire fluid content, for example, in a whole core sample, with a spatial resolution that is defined by a thickness of the standard sample that was used to determine the response map of the rf coil. The techniques can be applied to NMR data logging by continuously moving the NMR tool relative to the formation. For wireline logging, the tool moves from bottom to top of the targeted zone. For logging-while-drilling, the tool moves down from the top along with the drilling bit. The techniques described can be used to increase the spatial resolution to be smaller than the rf coil length. Increasing the spatial resolution can be done for high quality logging data without any additional cost because the data has already been acquired. The additional effort involves obtaining the response map of the rf coil of the tool. Elevated SNR can be obtained with slow logging speed.

The techniques described here can be implemented in medical applications for imaging. The techniques can reduce the use of PFG and provide a cheaper version of MRI instruments. The techniques can also reduce the noise generated by the application of PFG in MRI instruments.

Referring back to FIG. 1, the computer system 1002 can be used to provide computational functionalities associated with described algorithms, methods, functions, processes, flows, and procedures as described in this specification. The illustrated computer system 1002 is intended to encompass any computing device such as a server, desktop computer, laptop/notebook computer, wireless data port, smart phone, personal data assistant (PDA), tablet computing device, one or more processors within these devices, or any other suitable processing device, including both physical or virtual instances (or both) of the computing device. Additionally, the computer system 1002 may comprise a computer that includes an input device, such as a keypad, keyboard, touch screen, or other device that can accept user information, and an output device that conveys information associated with the operation of the computer system 1002, including digital data, visual, or audio information (or a combination of information), or a graphical user interface (GUI).

The computer system 1002 can serve in a role as a client, network component, a server, a database or other persistency, or any other component (or a combination of roles) of a computer system for performing the subject matter described in the instant specification. The illustrated computer system 1002 is communicably coupled with a network (not shown). In some implementations, one or more components of the computer system 1002 may be configured to operate within environments, including cloud-computing-based, local, global, or other environment (or a combination of environments).

At a high level, the computer system 1002 is an electronic computing device operable to receive, transmit, process, store, or manage data and information associated with the described subject matter. According to some implementations, the computer system 1002 may also include or be communicably coupled with an application server, e-mail server, web server, caching server, streaming data server, or other server (or a combination of servers).

The computer system 1002 can receive requests over a network (not shown) from a client application (for example, executing on another computer system 1002) and respond to the received requests by processing the said requests in an appropriate software application. In addition, requests may also be sent to the computer system 1002 from internal users (for example, from a command console or by other appropriate access method), external or third-parties, other automated applications, as well as any other appropriate entities, individuals, systems, or computers.

Each of the components of the computer system 1002 can communicate using a system bus. In some implementations, any or all of the components of the computer system 1002, both hardware or software (or a combination of hardware and software), may interface with each other or the interface 1004 (or a combination of both) over the system bus using an application programming interface (API) 1012 or a service layer 1013 (or a combination of the API 1012 and service layer 1013). The API 1012 may include specifications for routines, data structures, and object classes. The API 1012 may be either computer-language independent or dependent and refer to a complete interface, a single function, or even a set of APIs. The service layer 1013 provides software services to the computer system 1002 or other components (whether or not illustrated) that are communicably coupled to the computer system 1002. The functionality of the computer system 1002 may be accessible for all service consumers using this service layer. Software services, such as those provided by the service layer 1013, provide reusable, defined functionalities through a defined interface. For example, the interface may be software written in JAVA, C++, or other suitable language providing data in extensible markup language (XML) format or other suitable format. While illustrated as an integrated component of the computer system 1002, alternative implementations may illustrate the API 1012 or the service layer 1013 as stand-alone components in relation to other components of the computer system 1002 or other components (whether or not illustrated) that are communicably coupled to the computer system 1002. Moreover, any or all parts of the API 1012 or the service layer 1013 may be implemented as child or sub-modules of another software module, enterprise application, or hardware module without departing from the scope of this specification.

The computer system 1002 includes interface 1004. Although illustrated as a single interface 1004 in FIG. 1, two or more interfaces 1004 may be used according to particular needs, desires, or particular implementations of the computer system 1002. The interface 1004 is used by the computer system 1002 for communicating with other systems in a distributed environment, that are connected to the network (whether illustrated or not). Generally, the interface 1004 comprises logic encoded in software or hardware (or a combination of software and hardware) and operable to communicate with the network. More specifically, the interface 1004 may comprise software supporting one or more communication protocols associated with communications such that the network or interface's hardware is operable to communicate physical signals within and outside of the illustrated computer system 1002.

The computer system 1002 includes a processor 1005. Although illustrated as a single processor 1005 in FIG. 1, two or more processors may be used according to particular needs, desires, or particular implementations of the computer system 1002. Generally, the processor 1005 executes instructions and manipulates data to perform the operations of the computer system 1002 and any algorithms, methods, functions, processes, flows, and procedures as described in the instant specification.

The computer system 1002 also includes a database 1006 that can hold data for the computer system 1002 or other components (or a combination of both) that can be connected to the network (whether illustrated or not). For example, database 1006 can be an in-memory, conventional, or other type of database storing data consistent with this specification. In some implementations, database 1006 can be a combination of two or more different database types (for example, a hybrid in-memory and conventional database) according to particular needs, desires, or particular implementations of the computer system 1002 and the described functionality. Although illustrated as a single database 1006 in FIG. 1, two or more databases (of the same or combination of types) can be used according to particular needs, desires, or particular implementations of the computer system 1002 and the described functionality. While database 1006 is illustrated as an integral component of the computer system 1002, in alternative implementations, database 1006 can be external to the computer system 1002.

The computer system 1002 also includes a memory 1007 that can hold data for the computer system 1002 or other components (or a combination of both) that can be connected to the network (whether illustrated or not). For example, memory 1007 can be random access memory (RAM), read-only memory (ROM), optical, magnetic, and the like storing data consistent with this specification. In some implementations, memory 1007 can be a combination of two or more different types of memory (for example, a combination of RAM and magnetic storage) according to particular needs, desires, or particular implementations of the computer system 1002 and the described functionality. Although illustrated as a single memory 1007 in FIG. 1, two or more memories 1007 (of the same or combination of types) can be used according to particular needs, desires, or particular implementations of the computer system 1002 and the described functionality. While memory 1007 is illustrated as an integral component of the computer system 1002, in alternative implementations, memory 1007 can be external to the computer system 1002.

The application 1008 is an algorithmic software engine providing functionality according to particular needs, desires, or particular implementations of the computer system 1002, particularly with respect to functionality described in this specification. For example, application 1008 can serve as one or more components, modules, applications, or other components. Further, although illustrated as a single application 1008, the application 1008 may be implemented as multiple applications 1008 on the computer system 1002. In addition, although illustrated as integral to the computer system 1002, in alternative implementations, the application 1008 can be external to the computer system 1002.

There may be any number of computers 1002 associated with, or external to, a computer system containing computer system 1002, each computer system 1002 communicating over network. Further, the term "client," "user," and other appropriate terminology may be used interchangeably, as appropriate, without departing from the scope of this specification. Moreover, this specification contemplates that many users may use one computer system 1002, or that one user may use multiple computers 1002.

Figure 17:
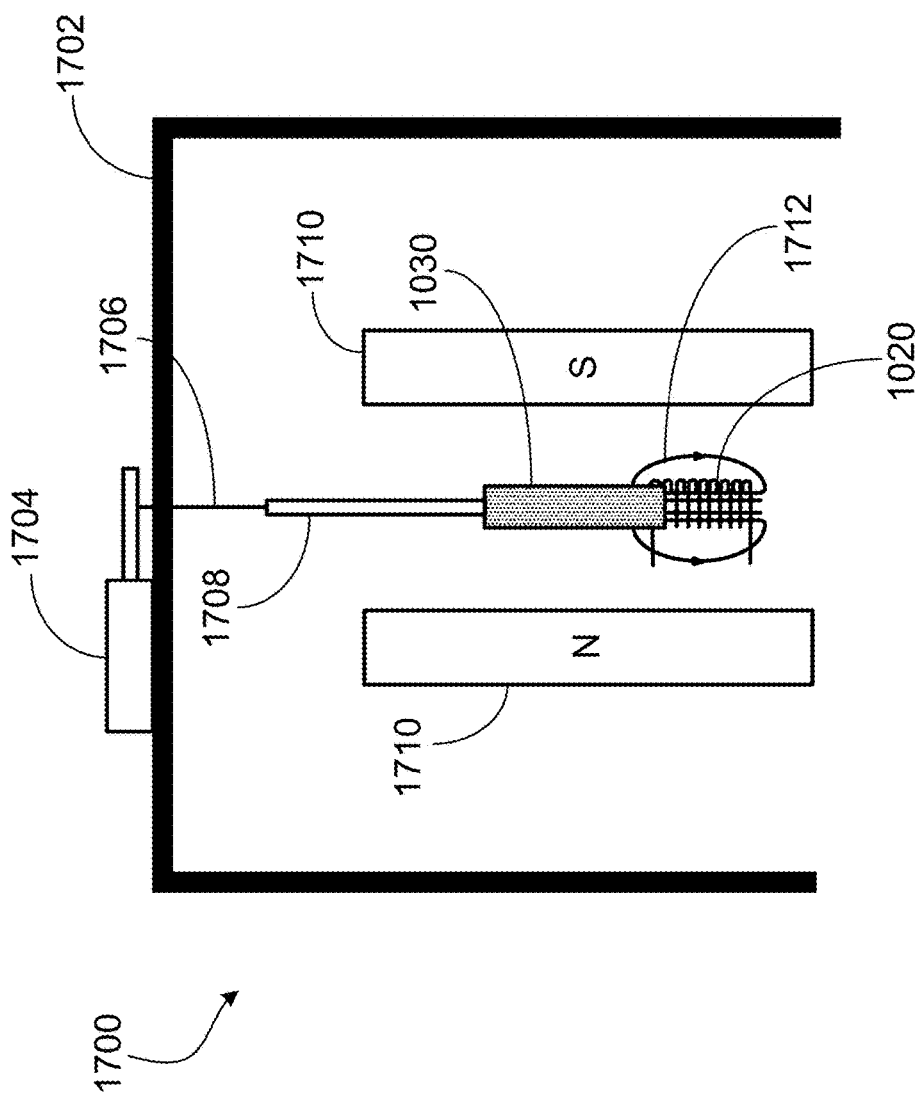
FIG. 17 is a schematic of a first arrangement to automatically move an NMR sample.

FIG. 17 is a schematic of a first arrangement 1700 to automatically move an NMR sample. In the first arrangement 1700, the NMR sample (for example, the NMR sample 1030) is surrounded by a support frame 1702. For example, the support frame 1702 can include at least two vertical members (such as two vertical plates), the top ends of which are connected by a horizontal member (such as a horizontal plate). A motor 1704 (for example, a step motor) is positioned on the support frame 1702, for example, above the horizontal member. The NMR sample 1030 is positioned below the horizontal member.

The motor 1704 includes a rotatable shaft that is powered by a power source and controlled by a controller. Using power from the power source, the controller can rotate the shaft in pre-defined steps. The horizontal member can include an opening (for example, a through hole) through which the motor 1704 is connected to the NMR sample 1030 through a connection member 1706. For example, the connection member is a ball-screw actuator (but other options are available for example, a chain, a rope, a tether or other cable) that can be affixed on one end to the rotatable shaft and on the other end to the sample holder 1708. That is, the connection member has sufficient strength to carry the weight of the NMR sample 1030 and the sample holder 1708. For example, the ball-screw actuator can be a rigid member that can be elevated and lowered using the motor 1704.

A non-magnetic sample holder 1708 is positioned between the connecting member 1706 and the NMR sample 1030. The sample holder 1708 can be a solid piece that connects to the sample and the connection member. The sample holder 1708 maintains the sample in a rigid position as the sample moves through the magnetic field, and keeps the motor and the connection member away from the sample. The sample holder 1708 can be made from Teflon, fused quartz, certain ceramics or other rigid non-magnetic $^1$H-free material ($^1$H is the isotope hydrogen-1). The NMR sample 1030 is positioned between two magnets 1710 of opposite poles.

In operation, the step motor 1704 can operate the actuator in predefined lengths, resulting in the NMR sample 1030 being raised or lowered, respectively, by pre-defined distances. After each pre-defined length, the step motor 1704 can stop moving the actuator and an NMR measurement can be made by subjecting the NMR sample 1030 to the NMR field 1712 generated by the NMR rf coil 1020. Alternatively, or in addition, the step motor 1704 can continuously move the actuator up or down, resulting in the NMR sample 1030 being raised or lowered, respectively, continuously. In such operation, NMR measurements can be taken continuously, that is, without stopping the NMR sample movement at the pre-defined distances. In such implementations, spatial resolution is determined by taking an average over a time step.

Figure 18:
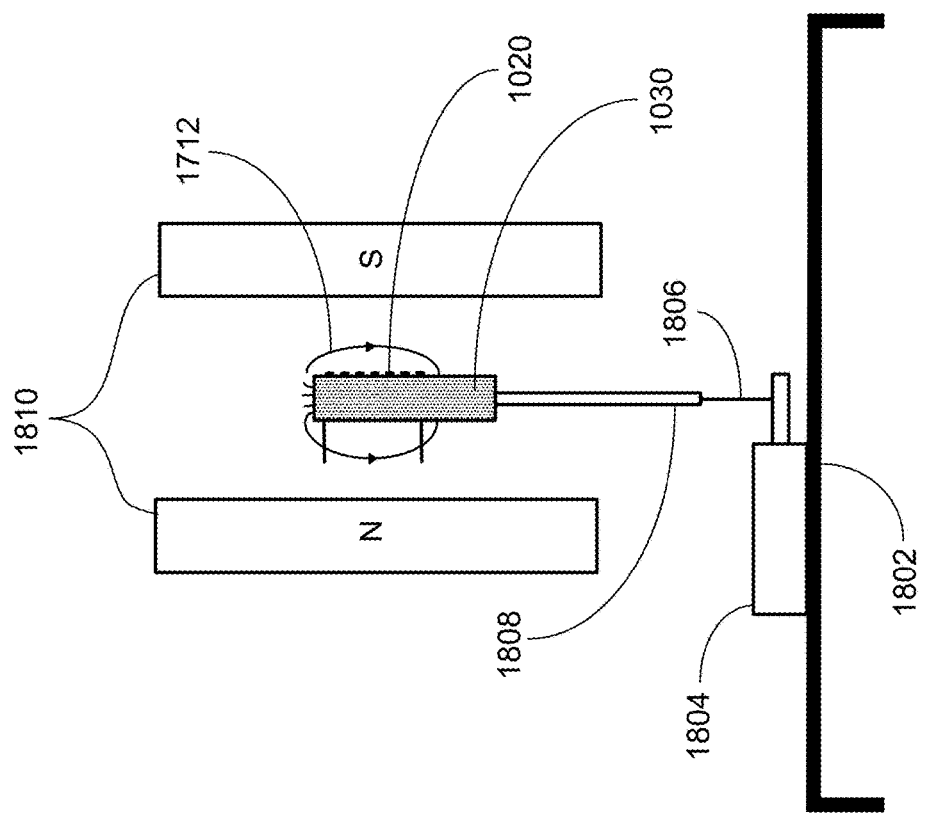
FIG. 18 is a schematic of a second arrangement to automatically move an NMR sample.

FIG. 18 is a schematic of a second arrangement 1700 to automatically move an NMR sample. In the second arrangement 1800, a support frame 1802 is positioned below the NMR sample (for example, the NMR sample 1030). For example, the support frame 1802 can include at least two vertical members (such as two vertical plates), the top ends of which are connected by a horizontal member (such as a horizontal plate). A motor 1804 (for example, similar to the motor 1704) is positioned on the support frame 1802, for example, above the horizontal member. The NMR sample 1030 is positioned above the support frame 1802.

The motor 1804 includes a rotatable shaft that is powered by a power source and controlled by a controller. Using power from the power source, the controller can rotate the shaft in pre-defined steps. The motor 1804 is connected to the NMR sample 1030 through a connection member 1806. For example, the connection member could be a ball-screw actuator that can be affixed on one end to the rotatable shaft and on the other end to the NMR sample holder 1808. A non-magnetic sample holder 1808 is positioned between the actuator and the NMR sample 1030. The NMR sample 1030 is positioned between two magnets 1810 of opposite poles. In the first arrangement 1700 and the second arrangement 1800, the motor 1704 and the motor 1804, respectively, are arranged to raise and lower the NMR sample 1030 vertically. In some implementations, described with reference to FIG. 19, a motor can be arranged to move the NMR sample 1030 horizontally, rather than vertically.

Figure 19:
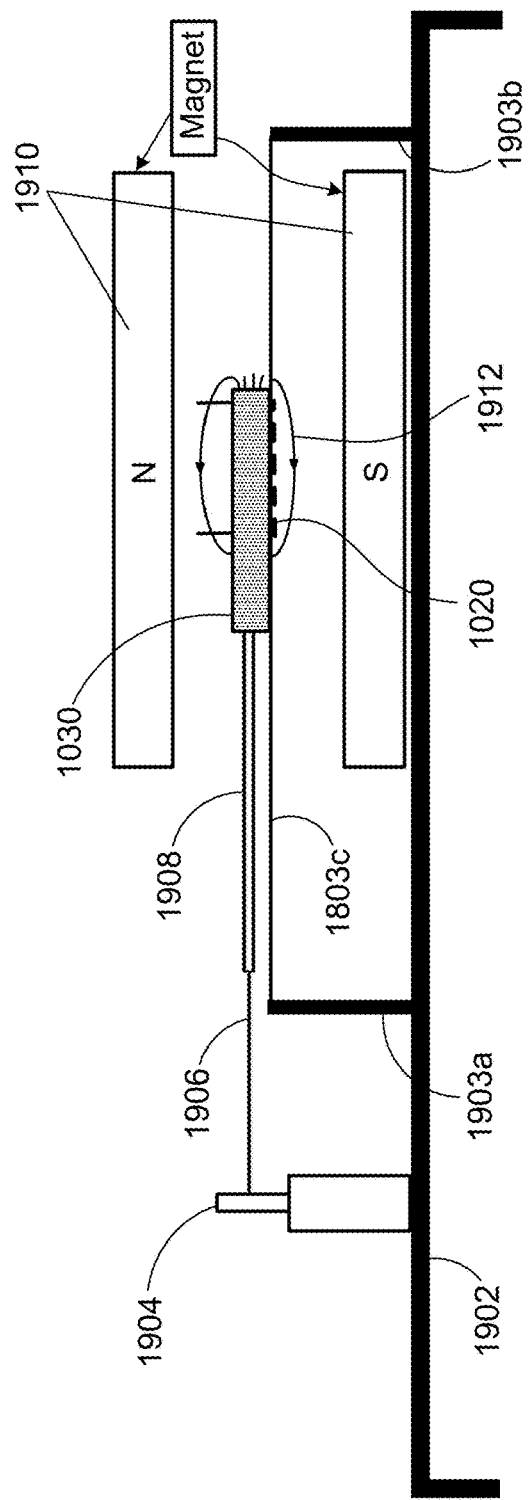
FIG. 19 is a schematic of a third arrangement to automatically move an NMR sample.

FIG. 19 is a schematic of a third arrangement 1900 to automatically move an NMR sample. In the third arrangement 1900, the NMR sample (for example, the NMR sample 1030) is positioned on a support frame 1902. For example, the support frame 1902 can include at least two vertical members (such as two vertical plates), the top ends of which are connected by a horizontal member (such as a horizontal plate). A motor 1904 (for example, similar to the motor 1704 or the motor 1804) is positioned on the support frame 1802, for example, above the horizontal member. The rotatable shaft of the motor 1904 can be oriented vertically, that is, perpendicular to the horizontal member.

The support frame 1902 can further include two vertical members 1903a and 1903b attached to the horizontal member. The two vertical members can be spaced apart by a distance that is at least equal to a total distance by which the NMR sample 1030 is to be moved. The two vertical members can be connected by a horizontal member 1903c that is attached to the top ends of the two vertical members. The NMR sample 1030 can be positioned on top of the horizontal member 1903c. The magnets 1910 can be positioned above and below the horizontal member 1903c with the NMR sample 1030 positioned between the magnets 1910.

The rotatable shaft of the motor 1904 is powered by a power source and controlled by a controller. The motor 1904 is connected to the NMR sample 1030 through a connection member 1906. For example, the connection member can be a ball-screw actuator that can be affixed on one end to the rotatable shaft and on the other end to the NMR sample holder 1908. A non-magnetic sample holder 1908 is positioned between the actuator and the NMR sample 1030.

In operation, the step motor 1904 can be operated to move the actuator by pre-defined lengths, resulting in the NMR sample 1030 being moved horizontally on the horizontal member 1903c either toward or away from the step motor 1904 by pre-defined distances. After each pre-defined length, the step motor 1904 can stop moving the actuator, and an NMR measurement can be made by subjecting the NMR sample 1030 to the NMR field 1712 generated by the NMR rf coil 1020. Alternatively, or in addition, the step motor 1904 can be operated to move the actuator continuously, resulting in the NMR sample 1030 being moved horizontally on the horizontal member 1903c continuously. In such operation, NMR measurements can be taken continuously, that is, without stopping the NMR sample movement at the pre-defined distances.

In some implementations, the arrangements can be combined. For example, the motor can be arranged such that the rotatable shaft is horizontal. The cable affixed on one end to the rotatable shaft can pass through a pulley, and turned (for example, by 90 degrees), and attached on the other end to a horizontally-oriented NMR sample. In such an arrangement, the vertical spooling and unspooling of the cable or actuator by the rotatable shaft can cause a horizontal movement of the sample. In another arrangement, the motor can be arranged such that the rotatable shaft is vertical. Using a pulley, the cable can be turned and affixed to a vertically-oriented NMR sample. In such an arrangement, a horizontal spooling and unspooling of the cable or actuator by the rotatable shaft can cause a vertical movement of the sample.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be useful.

What is claimed is:

1. A method comprising:
    performing Nuclear Magnetic Resonance (NMR) tests on a standard sample using a NMR radio frequency (rf) coil having a length;
    determining a response map for the NMR rf coil, the response map relating a plurality of relative NMR rf coil positions to a plurality of relative signal intensities, each relative NMR rf coil position corresponding to a respective signal intensity;
    performing the NMR tests using the NMR rf coil on a rock sample containing fluid, wherein a length of the rock sample is greater than the NMR rf coil; and
    determining a fluid content in the rock sample using results of the NMR tests using the NMR rf coil on the rock sample and using the response map for the NMR rf coil.

2. The method of claim 1, wherein a length of the standard sample is less than the length of the NMR rf coil, the standard sample has a known content of fluid, and performing the NMR tests on the standard sample using the NMR rf coil comprises performing the NMR tests at the plurality of relative NMR rf coil positions by, at each position:
    (a) positioning the standard sample within the NMR rf coil at a relative NMR rf coil position;
    (b) exposing the standard sample to an electromagnetic field; and
    (c) measuring a signal induced in the coil in response to the electromagnetic field, the signal corresponding to the known content of the fluid in the standard sample and the relative NMR rf coil position at which the standard sample is positioned, the signal corresponding to the relative signal intensity of the NMR rf coil position.

3. The method of claim 2, wherein performing the NMR tests at the plurality of relative NMR rf coil positions comprises:
    moving the standard sample within the NMR rf coil to a subsequent NMR rf coil position; and
    repeating steps (a), (b), and (c).

4. The method of claim 3, wherein the standard sample is moved automatically using a step motor.

5. The method of claim 3, wherein a distance by which the standard sample is moved within the NMR rf coil corresponds to a resolution at which the NMR rf coil determines the fluid content in the rock sample.

6. The method of claim 3, wherein determining the response map for the NMR rf coil comprises storing the relative NMR rf coil positions and the plurality of relative signal intensities in a computer-readable storage medium.

7. The method of claim 3, wherein performing the NMR tests using the NMR rf coil on the rock sample containing the fluid comprises, at each position:
    (d) positioning the rock sample within the NMR rf coil at a relative NMR rf coil position;

(e) exposing the rock sample to the electromagnetic field; and (f) measuring the signal induced in the coil in response to the electromagnetic field, the signal corresponding to the fluid content in the standard sample and the relative NMR rf coil position at which the rock sample is positioned.

8. The method of claim 7, wherein performing the NMR tests using the NMR rf coil on the rock sample containing the fluid comprises:

moving the rock sample within the NMR rf coil to the subsequent NMR rf coil position; and repeating steps (d), (e), and (f).

9. The method of claim 8, wherein the rock sample is moved automatically using a step motor.

10. The method of claim 7, wherein a distance by which the rock sample is moved within the NMR rf coil corresponds to a resolution at which the NMR rf coil determines the fluid content in the rock sample.

11. The method of claim 7, wherein determining the fluid content in the rock sample using results of the NMR tests using the NMR rf coil on the rock sample and using the response map for the NMR rf coil comprises implementing a post-processing protocol on a plurality of signal values measured at a plurality of NMR rf coil positions at which the rock sample was placed within the NMR rf coil, the post-processing protocol implementing the plurality of relative signal intensities measured at the plurality of NMR rf coil positions using the standard sample.

12. The method of claim 11, wherein implementing the post-processing protocol comprises:

representing the plurality of signal values in matrix form as S=RA, wherein S represents the plurality of signal values, R represents the plurality of relative signal intensities, and A represents a plurality of fluid content at the plurality of NMR rf coil positions; and determining A by implementing matrix-inversion.

13. The method of claim 11, wherein implementing the post-processing protocol comprises:

representing the plurality of signal values in matrix form as S=RA, wherein S represents the plurality of signal values, R represents the plurality of relative signal intensities, and A represents a plurality of fluid content at the plurality of NMR rf coil positions; and determining A by implementing convex minimization of an objective function.

14. A computer-implemented method comprising:

receiving a response map of a Nuclear Magnetic Resonance (NMR) radio frequency (rf) coil, the response map determined using NMR tests performed on a standard sample having a known length and fluid content using the NMR rf coil, the response map relating a plurality of relative NMR rf coil positions to a plurality of relative signal intensities, each relative NMR rf coil position corresponding to a respective relative signal intensity;

receiving a plurality of signal values determined by performing the NMR tests using the NMR rf coil on a rock sample containing fluid, wherein a length of the rock sample is greater than the NMR rf coil, wherein the NMR tests on the rock sample are performed by moving the rock sample within and relative to the NMR rf coil; and determining a fluid content in the rock sample using the plurality of signal values and the response map.

15. The method of claim 14, wherein determining the fluid content in the rock sample using the plurality of signal values and the response map comprises implementing a post-processing protocol on the plurality of signal values, the post-processing protocol implementing the plurality of relative signal intensities measured at the plurality of NMR rf coil positions using the standard sample.

16. The method of claim 15, wherein implementing the post-processing protocol comprises:

representing the plurality of signal values in matrix form as S=RA, wherein S represents the plurality of signal values, R represents the plurality of relative signal intensities, and A represents a plurality of fluid content at the plurality of NMR rf coil positions; and determining A by implementing matrix-inversion.

17. The method of claim 15, wherein implementing the post-processing protocol comprises:

representing the plurality of signal values in matrix form as S=RA, wherein S represents the plurality of signal values, R represents the plurality of relative signal intensities, and A represents a plurality of fluid content at the plurality of NMR rf coil positions; and determining A by implementing convex minimization of an objective function.

18. A system comprising:

a Nuclear Magnetic Resonance (NMR) system configured to perform NMR tests on samples, the NMR system comprising a NMR radio frequency (rf) coil configured to move relative to a sample to determine NMR signal values responsive to electromagnetic fields to which the sample is exposed; and a computer system comprising:

one or more processors; and a non-transitory computer-readable storage medium storing instructions executable by the one or more processors to perform operations comprising:

receiving a response map of the NMR rf coil, the response map determined using NMR tests performed by the NMR system on a standard sample having a known length and fluid content, the response map relating a plurality of relative NMR rf coil positions to a plurality of relative signal intensities, each relative NMR rf coil position corresponding to a respective relative signal intensity;

receiving a plurality of signal values determined by performing the NMR tests using the NMR system on a rock sample containing fluid, wherein a length of the rock sample is greater than the NMR rf coil, wherein the NMR tests on the rock sample are performed by moving the rock sample within and relative to the NMR rf coil; and determining a fluid content in the rock sample using the plurality of signal values and the response map.

19. The system of claim 18, wherein determining the fluid content in the rock sample using the plurality of signal values and the response map comprises implementing a post-processing protocol on the plurality of signal values, the post-processing protocol implementing the plurality of relative signal intensities measured at the plurality of NMR rf coil positions using the standard sample.

20. The system of claim 19, wherein implementing the post-processing protocol comprises:

representing the plurality of signal values in matrix form as S=RA, wherein S represents the plurality of signal values, R represents the plurality of relative signal intensities, and A represents a plurality of fluid content at the plurality of NMR rf coil positions; and determining A by implementing matrix-inversion.

21. The system of claim 19, wherein implementing the post-processing protocol comprises:
representing the plurality of signal values in matrix form as S =RA, wherein S represents the plurality of signal values, R represents the plurality of relative signal intensities, and A represents a plurality of fluid content at the plurality of NMR rf coil positions; and
determining A by implementing convex minimization of an objective function.

22. The system of claim 19, wherein a length of the standard sample is less than the length of the NMR rf coil, wherein the NMR system is configured to perform the NMR tests on the standard sample using the NMR rf coil by:
(a) positioning the standard sample within the NMR rf coil at a relative NMR rf coil position;
(b) exposing the standard sample to an electromagnetic field;
(c) measuring a signal induced in the coil in response to the electromagnetic field, the signal corresponding to the known content of the fluid in the standard sample and the relative NMR rf coil position at which the standard sample is positioned, the signal corresponding to the relative signal intensity of the NMR rf coil position;
moving the standard sample within the NMR rf coil to a subsequent NMR rf coil position; and
repeating steps (a), (b), and (c).

23. The system of claim 22, wherein the NMR system is configured to perform the NMR tests using the NMR rf coil on the rock sample containing the fluid by:
(d) positioning the rock sample within the NMR rf coil at a relative NMR rf coil position;
(e) exposing the rock sample to the electromagnetic field; and
(f) measuring the signal induced in the coil in response to the electromagnetic field, the signal corresponding to the fluid content in the standard sample and the relative NMR rf coil position at which the rock sample is positioned;
moving the rock sample within the NMR rf coil to the subsequent NMR rf coil position; and
repeating steps (d), (e), and (f).

24. The system of claim 22, wherein a distance by which the rock sample is moved within the NMR rf coil corresponds to a resolution at which the NMR rf coil determines the fluid content in the rock sample.

* * * * *